(12) United States Patent
Levine et al.

(10) Patent No.: US 7,062,328 B1
(45) Date of Patent: *Jun. 13, 2006

(54) SYSTEM AND METHOD FOR PROVIDING IMPROVED SPECIFICITY FOR AUTOMATIC MODE SWITCHING WITHIN AN IMPLANTABLE MEDICAL DEVICE

(75) Inventors: Paul A. Levine, Santa Clarita, CA (US); Mark W. Kroll, Simi Valley, CA (US); Scott Patrick Simon, Billings, MT (US)

(73) Assignee: Pacesetter, Inc., Sylmar, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/648,080

(22) Filed: Aug. 25, 2003

(51) Int. Cl.
*A61N 1/18* (2006.01)

(52) U.S. Cl. ...................................... 607/27
(58) Field of Classification Search .................. 607/5, 607/9, 14–16, 20, 27
See application file for complete search history.

(56) References Cited

U.S. PATENT DOCUMENTS

| | | | |
|---|---|---|---|
| 5,144,949 A | 9/1992 | Olson ................... 128/419 PG |
| 5,350,401 A | 9/1994 | Levine ........................ 607/4 |
| 5,441,523 A | 8/1995 | Nappholz .................... 607/4 |
| 5,549,649 A | 8/1996 | Florio et al. ................ 607/15 |
| 5,591,214 A | 1/1997 | Lu ................................ 607/9 |
| 5,720,295 A | 2/1998 | Greenhut et al. .......... 128/704 |
| 5,759,196 A | 6/1998 | Hess et al. ................. 607/14 |
| 5,792,192 A | 8/1998 | Lu ............................... 607/14 |
| 5,792,200 A | 8/1998 | Brewer ....................... 607/20 |
| 5,817,134 A | 10/1998 | Greenhut et al. ........... 607/14 |
| 5,951,593 A | 9/1999 | Lu et al. ..................... 607/14 |
| 6,128,533 A | 10/2000 | Florio et al. ................ 607/9 |
| 6,243,606 B1 * | 6/2001 | Mann et al. ................. 607/14 |
| 6,324,422 B1 | 11/2001 | Williams et al. .......... 600/510 |
| 6,351,669 B1 | 2/2002 | Hartley et al. ............... 607/5 |
| 6,519,493 B1 | 2/2003 | Florio et al. ................ 607/9 |
| 2002/0082661 A1 | 6/2002 | Plicchi et al. .............. 607/16 |

FOREIGN PATENT DOCUMENTS

| | | |
|---|---|---|
| EP | 0559847 B1 | 5/1997 |
| EP | 0904802 A2 | 3/1999 |
| EP | 0904802 A3 | 2/2000 |
| EP | 1038548 A2 | 9/2000 |

(Continued)

OTHER PUBLICATIONS

Levine, P.A. et al., "*Implementation of Automatic Mode Switching in Pacesetter's Trilogy DR+ and Affinity DR Pulse Generators*," Herzschr. Elektrophys. 10: Suppl. 1, I/46-I/57 (1999).

(Continued)

*Primary Examiner*—George Manuel

(57) ABSTRACT

Techniques for improving the specificity of automatic mode switching (AMS) are provided to prevent inappropriate mode switching and to ensure that mode switching is performed when needed. In one example, improved techniques for calculating a filtered rate interval (FARI) are provided, which help avoid inappropriate mode switching within devices that employ FARI in connection with the determination of the atrial rate. Also, techniques are provided for detecting atrial tachycardia and for distinguishing between a true tachycardia and a false tachycardia (such as pacemaker mediated tachycardia). The techniques described herein for detecting atrial tachycardia and for distinguishing between true and false tachycardia are advantageously employed in connection with AMS but may be used in other circumstances as well. Techniques employed in conjunction with dynamic atrial overdrive (DAO) pacing are also discussed.

6 Claims, 16 Drawing Sheets

FOREIGN PATENT DOCUMENTS

| | | |
|---|---|---|
| EP | 1038548 A3 | 3/2001 |
| EP | 1172125 A1 | 1/2002 |
| WO | WO 92/16258 | 10/1992 |
| WO | WO 97/11745 | 4/1997 |
| WO | WO 97/11747 | 4/1997 |

OTHER PUBLICATIONS

Barold, Serge S. et al., *"Pacemaker Repetitive Nonreentrant Ventriculoatrial Synchronous Rhythm. A Review,"* Journal of Interventional Cardiac Electrophysiology 5, 45-58 (2001).

* cited by examiner

SYSTEM AND METHOD FOR PROVIDING IMPROVED SPECIFICITY FOR AUTOMATIC MODE SWITCHING WITHIN AN IMPLANTABLE MEDICAL DEVICE

CROSS-REFERENCE TO RELATED APPLICATIONS

This application is related to copending U.S. patent applications: 1) Ser. No. 10/648,856, titled "System and Method for Providing Improved Specificity for Automatic Mode Switching Within an Implantable Medical Device"; and 2) Ser. No. 10/647,983, titled "System and Method for Providing Improved Specificity for Automatic Mode Switching Within an Implantable Medical Device", both applications filed Aug. 25, 2003.

FIELD OF THE INVENTION

The invention relates generally implantable cardiac stimulation devices, such as pacemakers and implantable cardioverter/defibrillators (ICDs), and in particular, to techniques for improving the specificity of automatic mode switching (AMS) techniques within such devices, i.e. for ensuring that mode switching occurs only when required.

BACKGROUND OF THE INVENTION

Pacemakers and ICDs carefully monitor characteristics of the heart such as the heart rate to detect arrhythmias, discriminate among different types of arrhythmias, identify appropriate therapy, and determine when to administer the therapy. The device tracks the heart rate by examining electrical signals that result in the contraction and expansion of the chambers of the heart. The contraction of atrial muscle tissue is triggered by the electrical depolarization of the atria, which is manifest as a P-wave in a surface electrocardiogram (ECG) and as a rapid deflection (intrinsic deflection) in an intracardiac electrogram (IEGM). The contraction of ventricular muscle tissue is triggered by the depolarization of the ventricles, which is manifest on the surface ECG by an R-wave (also referred to as the "QRS complex") and as a large rapid deflection (intrinsic deflection) within the IEGM. The electrical activation detected by the pacemaker on either the atrial or ventricular channel is the intrinsic deflection arising from that specific chamber. Repolarization of the ventricles is manifest as a T-wave in the surface ECG and a corresponding deflection in the IEGM. A similar depolarization of the atrial tissue usually does not result in a detectable signal within either the surface ECG or the IEGM because it coincides with and is obscured by the R-wave. Note that, strictly speaking, the terms P-wave, R-wave and T-wave typically refer only to features of the surface ECG. Herein, however, for the sake of brevity and generality, the terms will be used to also refer to the corresponding signals as sensed internally. Also, where an electrical signal is generated in one chamber but sensed in another, it is referred to herein, where needed, as a "far-field" signal. Hence, a P-wave sensed in the ventricles is referred to as a far-field P-wave. An R-wave sensed in the atria is a far-field R-wave (FFRW).

The sequence of electrical events that represent P-waves, followed by R-waves (or QRS complexes), followed by T-waves can be detected within IEGM signals sensed using pacing leads implanted inside the heart. To help prevent misidentification of electrical events and to more accurately detect the heart rate, the stimulation device employs one or more refractory periods and blanking periods. Within a refractory period, the device does not process electrical signals during a predetermined interval of time—either for all device functions (an absolute refractory period) or for selected device functions (a relative refractory period). As an example of a refractory period, upon detection of an R-wave on a ventricular sensing channel (or upon delivery of a V-pulse to the ventricles), a Post-Ventricular Atrial Refractory Period (PVARP) is initiated on an atrial sensing channel. A first portion of the PVARP comprises a post ventricular atrial blanking (PVAB) interval wherein the pacemaker can detect signals on the atrial channel but does not use the signals for any purpose. The PVAB is provided to prevent the device from erroneously responding to a far-field R-wave on the atrial channel. The PVARP concludes with a relative refractory period during which the pacemaker continues to ignore all signals detected on the atrial channel as far as the triggering or inhibiting of pacing functions is concerned, but not for other functions, such as detecting rapid atrial rates or recording diagnostic information. A total atrial refractory period (TARP) is defined as the period of time including an atrioventricular AV delay, any AV delay extension and the PVARP. The sum of the AV delay and the PVARP define the fastest atrial rate that can be detected to still trigger a ventricular output in a 1:1 relationship.

Accurate detection of heart rates is required, for example, for the purposes of enabling an AMS system wherein the pacemaker switches from a tracking mode such as a DDD mode to a non-tracking mode such as VDI or DDI mode. More specifically, the pacemaker compares a current atrial rate with an atrial tachycardia detection threshold (ATDR) and, if it exceeds the threshold, atrial tachycardia is assumed and the pacemaker switches from the tracking mode to the non-tracking mode. Details regarding AMS may be found in the following patents: U.S. Pat. Nos. 5,441,523 and 5,591,214, which are incorporated herein by reference. See also Levine et al., "Implementation Of Automatic Mode Switching In Pacesetter's Trilogy DR+ And Affinity DR Pulse Generators", Herzschr. Elektrophys. 10 (1999) 5, S46–S57. Note that DDD, VDI, VVI and DDI are standard device codes that identify the mode of operation of the device. DDD indicates a device that senses and paces in both the atria and the ventricles and is capable of both triggering and inhibiting functions based upon events sensed in the atria and the ventricles. VVI indicates that the device is capable of pacing and sensing only in the ventricles but is only capable of inhibiting the functions based upon events sensed in the ventricles. VDI is identical to VVI except that it is also capable of sensing intrinsic atrial activity. DDI is identical to DDD except that the device is only capable of inhibiting functions based upon sensed events, rather than triggering functions. As such, the DDI mode is a non-tracking mode precluding it from triggering ventricular outputs in response to sensed atrial events. Numerous other device modes of operation are possible, each represented by standard abbreviations of this type.

Thus, an AMS system recognizes when the patient is in an atrial tachycardia such as atrial fibrillation (AF) and switches from the tracking mode to the non-tracking mode to prevent the device from attempting to track the high atrial rates associated with AF. The aforementioned TARP normally prevents the recognition of very rapid atrial rates. However, to facilitate recognition of high atrial rates, the pacemaker can be configured to detect atrial events that coincide with the relative refractory portion of the PVARP. To reduce the likelihood of switching from a tracking mode to a non-tracking mode based on isolated atrial premature beats or a nonsustained run of supraventricular tachycardia (SVT), the AMS system preferably utilizes an averaging technique referred to as a filtered atrial rate interval (FARI) in which all atrial events are counted, including both sensed and paced atrial events, whether captured or not. Filtered atrial rate techniques are discussed in U.S. Pat. No. 5,549,649 to Florio, et al., entitled "Programmable Pacemaker Including an Atrial Rate Filter for Deriving a Filtered Atrial Rate Used for Switching Pacing Modes" and in U.S. Pat. No. 6,128,533 also to Florio, et al., entitled "Pacemaker With Automatic PVARP Adjustment During Automatic Mode Switching", which are both incorporated by reference herein.

Whereas AMS provides a technique for recognizing an atrial tachycardia should one arise, other techniques have been developed for preventing an atrial tachycardia from occurring. One such technique, referred to as dynamic atrial overdrive (DAO) pacing, is described in U.S. Pat. No. 6,519,493 to Florio et al., entitled "Methods And Apparatus For Overdrive Pacing Heart Tissue Using An Implantable Cardiac Stimulation Device". With DAO, the pacing device artificially paces the atria at an overdrive rate set to be slightly faster than the intrinsic atrial rate of the patient. It is believed that overdrive pacing helps prevent the onset of atrial tachycardia in part by reducing the number of ectopic beats, i.e. atrial heart beats that do not arise from normal sinus pulses. The DAO pacing rate is controlled to remain generally uniform with the rate is adjusted upwardly or downwardly in response to native sinus or atrial ectopic beats in an effort to prevent the occurrence of atrial fibrillation and other atrial tachyarrhythmias. For the purpose of this discussion, atrial tachycardias and atrial fibrillation shall be used synonymously and interchangeably and refer to any pathologic atrial tachycardia or atrial rate that exceeds the programmed atrial tachycardia detection rate (ATDR). Capture of overdrive pulses may be verified as set forth in U.S. patent application Ser. No. 10/138,438, of Bradley et al., entitled "Method And Apparatus For Providing Atrial Auto-Capture In A Dynamic Atrial Overdrive Pacing System For Use In An Implantable Cardiac Stimulation Device", filed May 2, 2002. The aforementioned patent and patent application are incorporated herein as well.

Thus, DAO provides a technique for preventing the onset of an atrial tachycardia and, should one nevertheless arise, AMS provides a technique for switching to a non-tracking mode so that the high atrial rate is not tracked. DAO is preferably active at all times while the pacemaker is in the tracking mode and is deactivated in the non-tracking mode. Although DAO and AMS are both effective tools, certain problems arise when implemented together. In particular, the following situation may arise. A nonsustained salvo of SVT or multiple atrial ectopic beats can cause the DAO system to increase the atrial pacing rate. On the cycle before release of the next atrial output pulse, an atrial premature beat coincides with the PVARP sufficiently early that it does not conduct to the ventricle. This P-wave is detected by the microprocessor and used to decrement the FARI value, i.e. the detected P-wave causes the rate defined by the FARI to be incremented, which shortens the actual FARI since rate and interval have an inverse relationship. However, since the P-wave coincides with the PVARP, it does not alter the timing interval and thus does not delay release of the next atrial pulse (A-pulse). If the atrial pulse is delivered at a time when the atrial myocardium is physiologically refractory, it will be ineffective. Then, if at the end of the AV delay, a ventricular output (V-pulse) is delivered and captured, the ventricular output can initiate a retrograde P-wave (PR-wave). With the PVARP programmed appropriately to prevent development of a pacemaker mediated tachycardia (PMT), the retrograde P-wave is then not used to trigger a ventricular pulse but is instead used to further adjust the FARI value. The subsequent atrial pulse is again ineffective.

This results in a rhythm termed "repetitive nonreentrant ventriculo-atrial synchronous rhythm" (RNRVAS), which has been described in detail in a paper by Barold and Levine, Journal of Interventional Cardiac Electrophysiology 2001; 5: 45–58 and also described in U.S. patent application Ser. No. 09/795,265 entitled "Implantable Cardiac Device Providing Repetitive Non-Reentrant Ventriculoatrial Synchronous (RNRVAS) Rhythm Therapy Using VA Interval Extension And Method", of Levine et al., filed Aug. 29, 2002, which is incorporated by reference herein.

In addition, note that a true PMT means that there is a real atrial depolarization that is detected during the atrial alert period. Though retrograde, it is still present. Hence, it will inhibit release of an atrial output pulse even if it were to increase the potential atrial paced rate in accord with DAO. If a Maximum Sensor Rate is set higher than a Maximum Tracking Rate (MTR), then DAO can cause atrial pacing at a rate higher than the MTR and again precipitate a RNRVAS rhythm. RNRVAS rhythm can result in adverse symptoms such as a significant decrease in both blood pressure and cardiac output, palpitations, dizziness and lightheadedness and hence should be avoided.

As a result of RNRVAS, a series of atrial events can arise wherein the pacemaker interprets the rhythm as a tachycardia and initiates mode switching. A—A and $P_R$—$P_R$ intervals may each occur at a normal rate (where the A—A interval is the interval between consecutive A-pulses and the $P_R$—$P_R$ interval is the interval between consecutive $P_R$-waves.) The pacemaker, as noted, utilizes all usable atrial events (paced and sensed) in the calculation of the FARI value. Hence, as far as the pacemaker is concerned, the actual atrial rates are a combination of the $A_{(ineffective)}$–$P_{(retrograde)}$ and the $P_{(retrograde)}$–$A_{(ineffective)}$ intervals. The effect can double the actual rate. Then, when the atrial rate calculated based on the FARI exceeds the ATDR, an inappropriate mode switch occurs and the system exits DAO.

Accordingly, it would be desirable to provide improved FARI techniques for avoiding inappropriate mode switching, particularly as a result of RNRVAS, and aspects of the invention are directed to that end. Note that the techniques described in U.S. patent application Ser. No. 09/795,265 are directed to preventing or detecting the onset and terminating RNRVAS. Techniques of the present invention are instead directed to preventing inappropriate mode switching should RNRVAS occur and may be employed in circumstances wherein RNRVAS detection and termination techniques are not effective or may be employed in devices not configured to provide for RNRVAS detection.

Periods of rapid atrial pacing can also occur in the setting of normal rate modulated behavior even in the absence of DAO. Then, if a premature ventricular complex (PVC) occurs and conducts retrograde or an early atrial premature complex (APC) occurs coinciding with the PVARP and not conducting in an anterograde direction (from atrium to the ventricle through the normal conduction pathway) and if retrograde conduction is intact, an RNRVAS rhythm may occur. As with DAO, the sustained Pr (ineffective)-A-output interval and subsequent $A_{(ineffective)}$-Pr interval may trigger inappropriate AMS by falsely shortening the FARI causing the detected "atrial" rate to exceed the ATDR. This invention will address this setting as well and will be applicable to devices where DAO is either not available or had not been enabled.

Thus, RNRVAS can result in a situation wherein an atrial tachycardia is detected and a mode switch occurs when, in fact, no true atrial tachycardia is actually present. Circumstances can also arise wherein a true atrial tachycardia has occurred but remains undetected. For example, during a true atrial tachycardia, the amplitudes of the P-waves are sometimes too low to be detected based on the currently programmed atrial sensitivity, and so the atrial tachycardia remains undetected. Accordingly, it would also be desirable to provide improved techniques for detecting the onset of an atrial tachycardia to ensure proper mode switching and further aspects of the invention are directed to that end. In addition, as noted, circumstances can arise wherein a mode switch to the non-tracking mode is performed even though a true atrial tachycardia has not occurred. Accordingly, it would also be desirable to provide improved techniques for verifying that a true atrial tachycardia has occurred and still further aspects of the invention are directed to that end. By providing the foregoing, improved specificity of AMS is thereby achieved.

SUMMARY

Various techniques are provided for improving the specificity of AMS within implanted cardiac stimulation devices to prevent inappropriate mode switching and to ensure that mode switching is performed when needed. Included are improved techniques for detecting the onset of atrial tachycardia, particularly AF, and for distinguishing a true atrial tachycardia from a false atrial tachycardia such as FFRW sensing or RNRVAS. The techniques for detecting atrial tachycardia and for distinguishing between true and false tachycardia are advantageously employed in connection with AMS but may be used in other circumstances as well.

In accordance with a first general aspect of the invention, FARI-based techniques are provided to prevent inappropriate mode switching caused by the onset of RNRVAS. In one technique, if atrial capture verification is not available, the FARI value used by the AMS system to control mode switching is derived based only on intrinsic atrial events—rather than on intrinsic atrial events and atrial-paced events. In another technique, wherein atrial capture verification is available, the FARI value is derived based only on a combination of intrinsic atrial events and captured atrial pulses. By excluding either all atrial-paced events or at least all non-captured atrial-paced events, the aforementioned sequence of events triggering inappropriate mode switching as a result of onset RNRVAS is substantially avoided. This technique may be employed either while DAO is performed or otherwise.

In accordance with a second general aspect of the invention, techniques are provided for detecting atrial tachycardia such as AF. In a first technique, loss of capture detection is used to trigger a search for low amplitude intrinsic atrial events indicative of possible atrial tachycardia. Briefly, atrial events are detected based on an initial atrial sensitivity level and atrial pacing pulses are selectively delivered to the atria. Upon detection of loss of capture of atrial pulses, the atrial sensitivity level is increased to allow for detection of low-amplitude atrial events and a determination is made whether the low-amplitude events are true intrinsic atrial events or far-field ventricular events. This determination may be made, for example, by examining the degree of variability among intervals separating the atrial events from known ventricular events. If the degree of variability is sufficient, the atrial events are deemed to be true intrinsic events and further atrial outputs are inhibited due to possible atrial tachycardia. In this manner, not only can a possible atrial tachycardia be detected but the FARI interval can be more properly derived to achieve improved AMS mode switching.

In a second atrial tachycardia detection technique, detection of a sequence of alternating atrial events is used to trigger a search for low amplitude intrinsic events indicative of possible atrial tachycardia. Briefly, upon detection of an alternating sequence of paced and sensed atrial events, the atrial sensitivity level is increased to allow for detection of additional low-amplitude atrial events. Again, a determination is made whether the low-amplitude events are true intrinsic atrial events or far-field ventricular events. Increasing the atrial sensitivity may predispose to FFRW detection but the stability of the relationship between the newly identified signal and the preceding paced or sensed ventricular event will identify this complex as a FFRW allowing it to be ignored. If the low-amplitude events are deemed to be true intrinsic atrial events, further atrial outputs are inhibited due to possible atrial tachycardia. Otherwise, the events are simply ignored in further atrial calculations such as in deriving the FARI interval. Again, not only can a possible atrial tachycardia be detected but the FARI interval can be more properly derived.

In a third atrial tachycardia detection technique, detection of a particular pattern of events is use to detect a possible tachycardia. Briefly, a pattern of atrial events is monitored and compared against a set of stored patterns representative of one or more of: a true atrial tachycardia; a false atrial tachycardia; an atrial loss of capture at high rate; or an atrial bigeminy/RNRVAS. Appropriate steps are then taken. For example, if a false tachycardia is detected while the device is currently non-tracking, the device switches back to the tracking mode. If a true tachycardia is detected while the device is currently tracking, the device switches to the non-tracking mode. If atrial loss of capture is detected, the atrial pulse magnitude is preferably slowed so as to allow more time for the atrial physiologic refractory period to recover to thereby avoid loss of capture due to physiologic refractoriness. If atrial loss of capture continues to occur, the pulse magnitude is then increased. In this manner, pattern matching allows various conditions to be detected and promptly addressed.

In a fourth atrial tachycardia detection technique, verification of a true atrial tachycardia is performed in a non-tracking mode based on the atrial rate. Briefly, upon the atrial rate exceeding some threshold, the AMS system switches to the non-tracking mode. The high atrial rate may be indicative of a true atrial tachycardia or may arise for other reasons. To determine whether a true atrial tachycardia is occurring, if the frequency of atrial pulses exceeds some paced-beat threshold, the atrial sensitivity is increased to detect low amplitude P-waves indicative of a true atrial tachycardia. If the frequency of detected P-waves then exceeds a sensed-beat threshold, the presence of a true atrial tachycardia is thereby verified. This technique is performed primarily for confirmatory purposes and if a true atrial tachycardia is not present, the system exits AMS and returns to the tracking mode.

Thus, various techniques are provided for avoiding inappropriate mode switching as a result of RNRVAS, for confirming the presence of an atrial tachycardia while in a nontracking mode, and for verifying that a true atrial tachycardia has occurred. Each helps improve the specificity of AMS. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Stimulation Device

Figure 1:
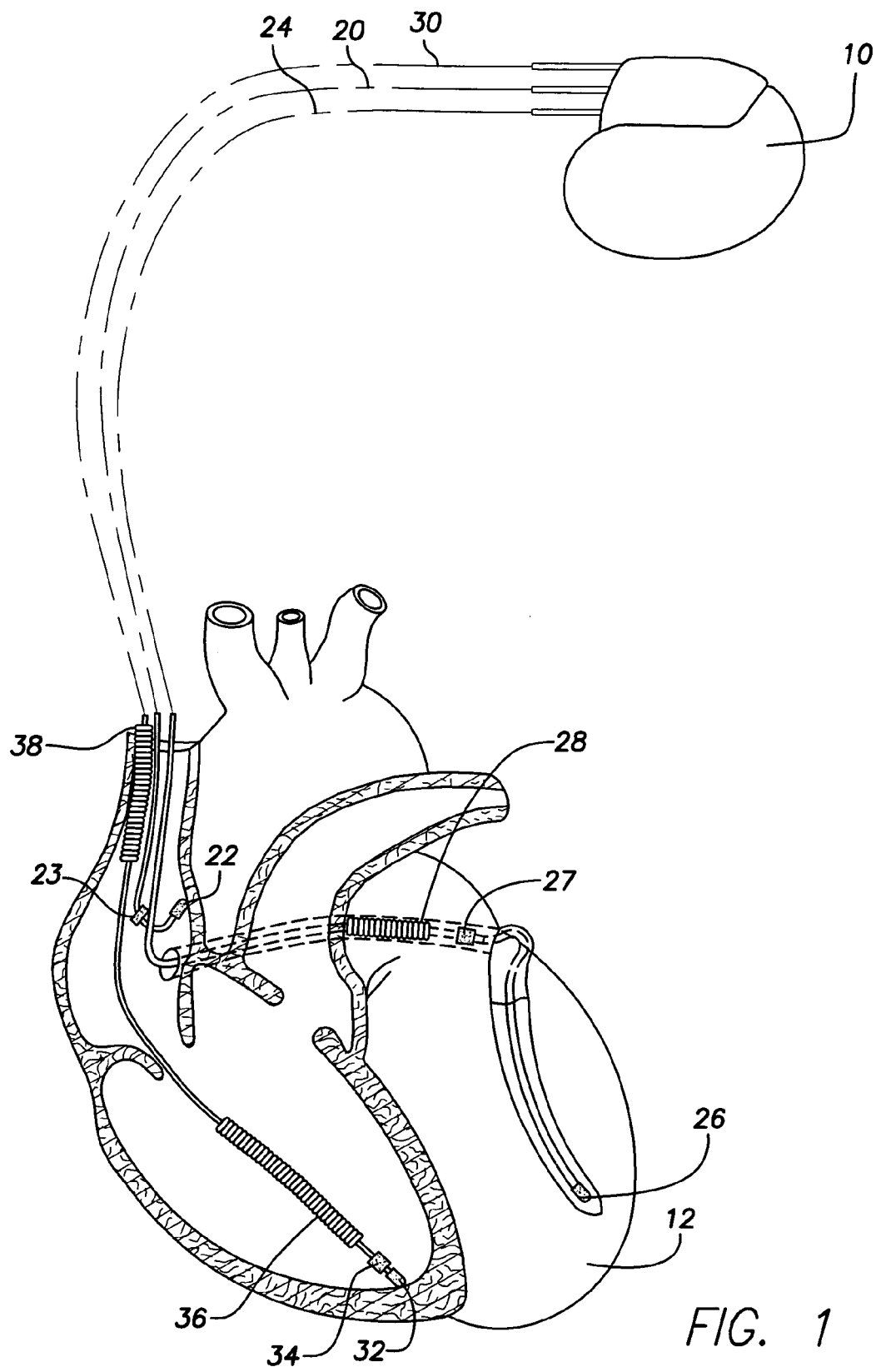
FIG. 1 is a simplified, partly cutaway view illustrating an implantable stimulation device in electrical communication with at least three leads implanted into a patient heart for delivering multi-chamber stimulation and shock therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle.

Figure 2:
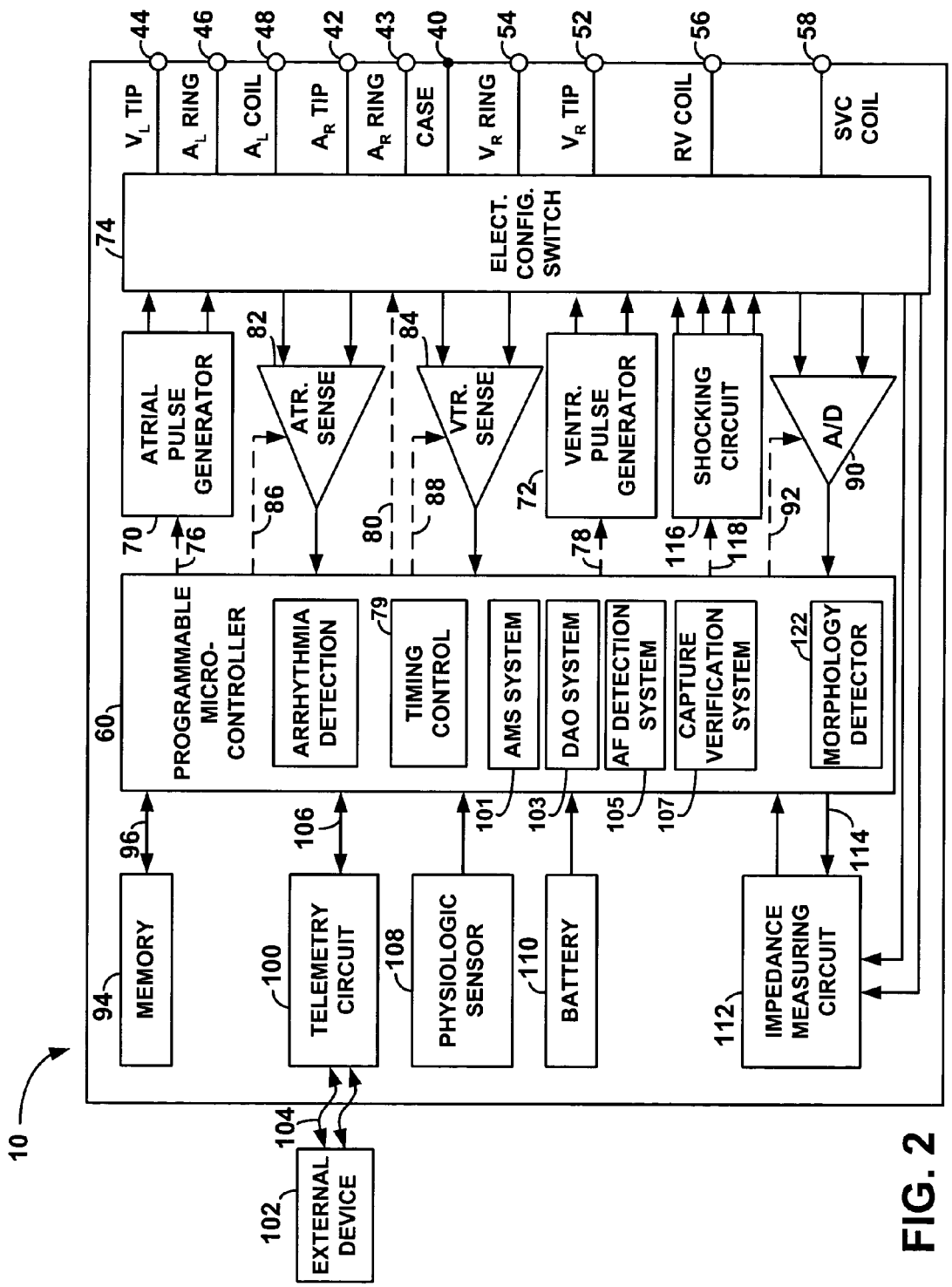
FIG. 2 is a functional block diagram of the multi-chamber implantable stimulation device of FIG. 2, illustrating the basic elements that provide cardioversion, defibrillation and/or pacing stimulation in four chambers of the heart and particularly illustrating AMS, DAO, FARI, automatic capture verification and AF detection systems.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry (not separately shown) used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Figure 3:
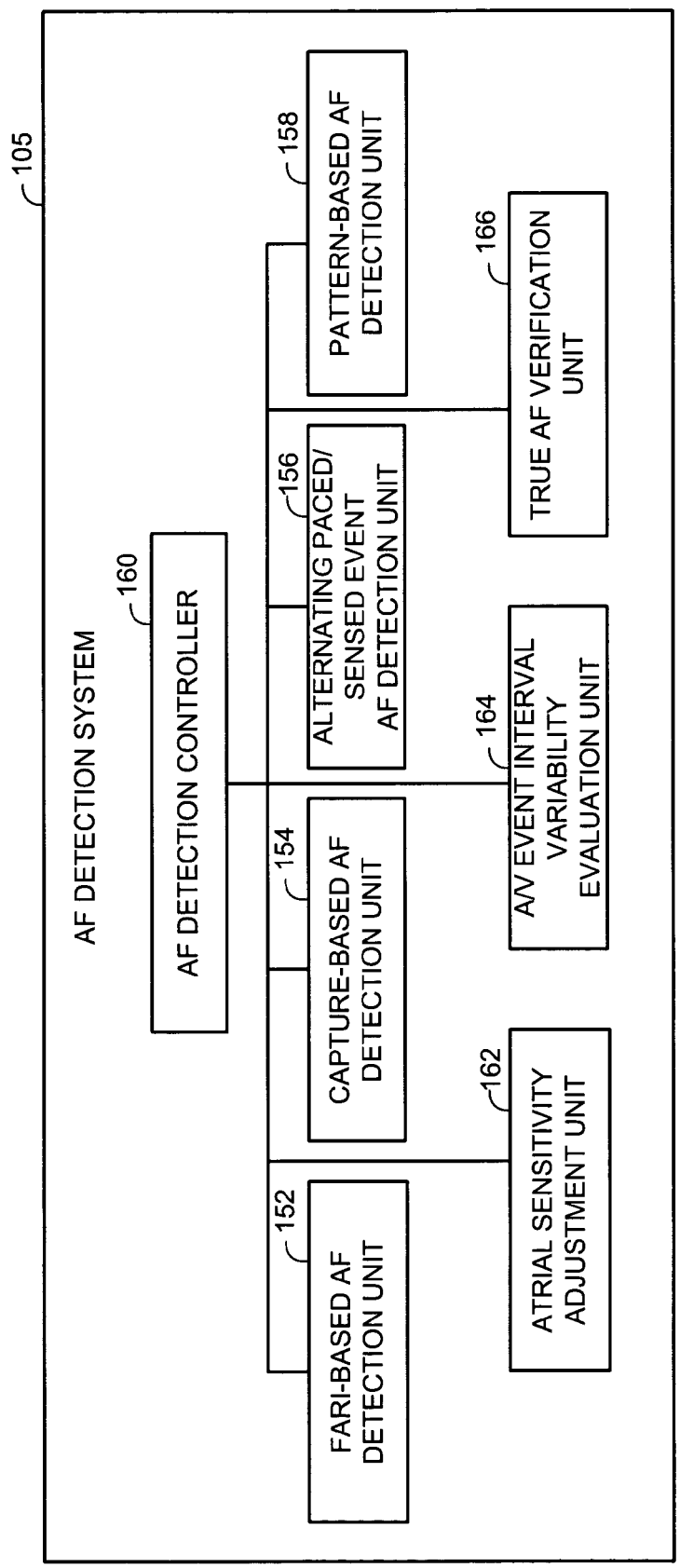
FIG. 3 is a functional block diagram of components of the AF detection system of FIG. 2.

The microcontroller also includes: an AMS system 101; a DAO system 103; an AF detection system 105; and a capture verification system 109. Individual components of AF detection system 105 are shown in FIG. 3. Briefly, AMS system controls automatic switching from a tracking mode to a non-tracking mode in response to detection of AF by the AF detection system. AF may be detected in accordance with FARI-based techniques, capture-based techniques, alternating event-based techniques or other pattern-based techniques. At all times while in the tracking mode, the system preferably performs DAO pacing under the control of the DAO system. If capture-based detection of AF is employed, capture is verified using the capture verification system. A technique for implementing automatic capture verification during DAO pacing is described in the aforementioned patent application of Bradley et al. Finally, while in the non-tracking mode, the microcontroller also preferably operates to detect whether a true atrial tachycardia has occurred using additional components of the AF detection system. The operations of the AMS system, the DAO system, the AF detection system, and the capture verification system are described in greater detail below with reference to FIGS. 3–18. Finally, though each is shown as being a component of the microcontroller, some or all of may be implemented separately from the microcontroller.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. The battery 110 may vary depending on the capabilities of the device 10. If the system only provides low voltage therapy, a lithium iodine or lithium copper fluoride cell may be utilized. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 is preferably capable of high voltage therapy and employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules) or high energy (11 to 40 joules), as controlled by the microcontroller 60. Such shocking pulses are applied to the heart of the patient through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generated under the control of AF suppression unit 101. The fibrillation shocks are generated under the control of other components of microcontroller 60, not separately shown. Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Overview of AF Detection System

FIG. 3 illustrates pertinent components of AF detection system 105 of FIG. 2. In particular, the AF detection system includes a FARI-based detection unit 152, a capture-based AF detection unit 154, an alternating paced/sensed event AF detection unit 156, and a pattern-based AF detection unit 158. In many implementations, only a single one of the various AF detection units is provided, thus providing AF detection in accordance with only a single AF detection technique. Four separate AF detection units are illustrated in FIG. 3 for the sake of the generality and completeness. If multiple AF detection units are implemented, an AF detection controller 160 selects one of the detection units for use in detecting AF pursuant to programming commands received from an external programmer or pursuant to any pre-programming of the implantable device.

Briefly, the FARI-based detection unit utilizes otherwise conventional FARI techniques to detect the onset of possible AF but modified so as to count only atrial-sensed events (if capture verification is not employed) or both atrial-sensed and atrial-paced events (if capture verification is employed.) The FARI-based techniques are described in greater detail below with reference to FIGS. 4–10. The capture-based AF detection unit operates to detect the onset of possible AF following loss of capture by increasing the atrial sensitivity using sensitivity adjustment unit 162 then evaluating the variability in intervals between atrial and ventricular events using variability evaluation unit 164. The capture-based AF detecting technique is described in greater detail below with reference to the FIG. 11. Alternating event AF detection unit operates to detect the onset of possible AF following detection of alternating paced and sensed atrial events also by increasing the atrial sensitivity and then evaluating the variability of atrial/ventricular events intervals. The alternating event-based AF detection technique is described in greater detail below with reference to the FIG. 15. The pattern-based AF detection unit operates to detect the onset of possible AF and certain other arrhythmias based upon the occurrence of selected patterns of events, in accordance with techniques to be described in greater detail below with reference to FIG. 16. Furthermore, the AF detection system also includes a true AF verification unit 166, which operates to verify the occurrence of a true AF while in the non-tracking mode, in accordance with techniques to be described in greater detail below with reference to FIG. 18. Hence, regardless of the particular technique used to detect the onset of possible AF, the true AF verification unit determines whether a true atrial tachycardia has, in fact, occurred. This is primarily performed for diagnostic purposes.

Referring to the remaining figures, flow charts provide an overview of the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

FARI-Based Techniques for Avoiding Inappropriate Mode Switches

Figure 4:
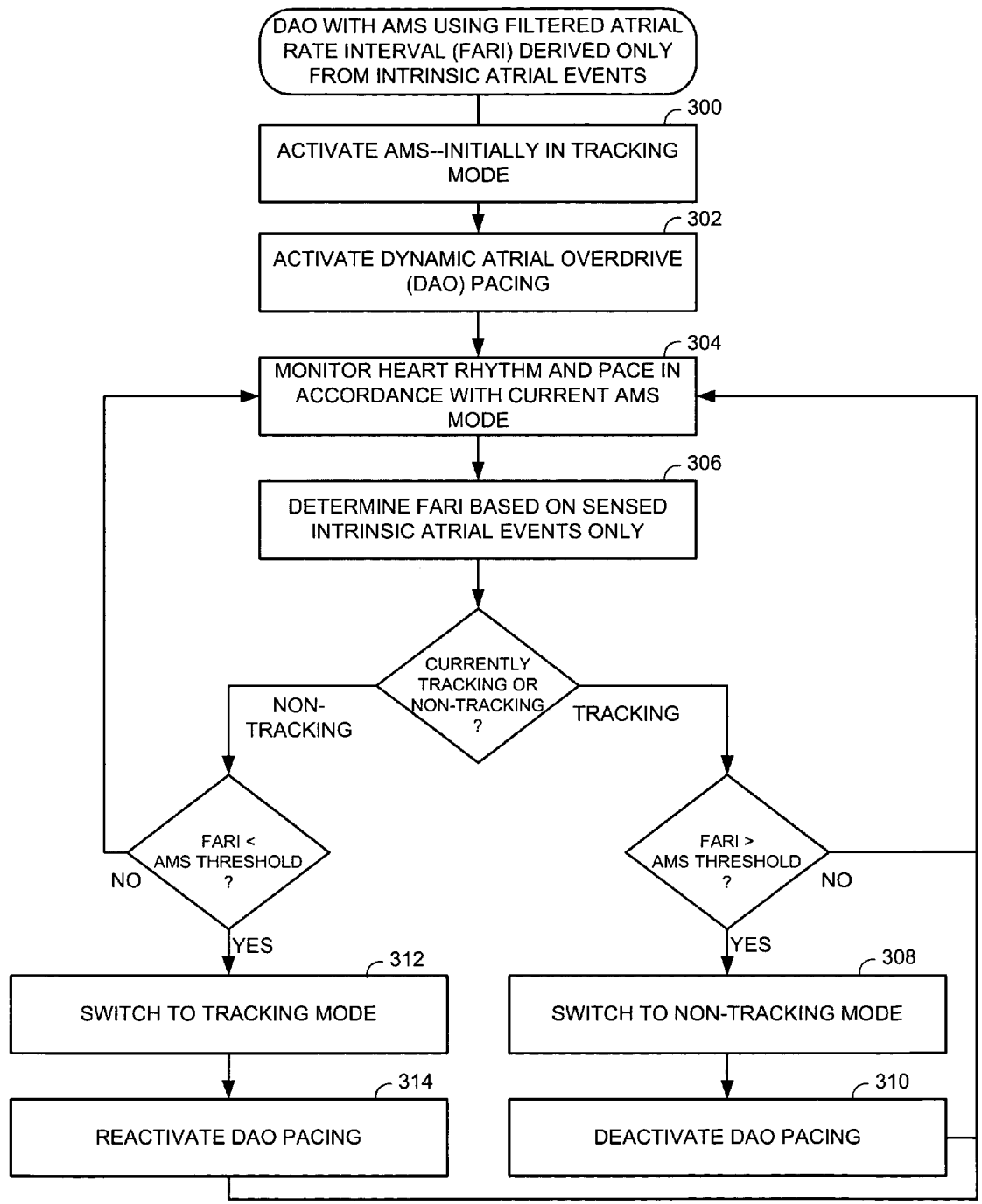
FIG. 4 is a flow chart illustrating the manner by which the microcontroller of FIG. 2 controls the FARI system during DAO to calculate a FARI value using only atrial-sensed events so as to reduce risk of inappropriate mode switching by the AMS system caused by RNRVAS during DAO.

Referring now to FIGS. 4–11, improved FARI calculation techniques will now be described for use in avoiding inappropriate mode switching. Referring first to FIG. 4, the microcontroller activates the AMS system (FIG. 2), at step 300, to control mode switching and activates the DAO system (also FIG. 2), at step 302, to control overdrive pacing. AMS is initially activated in the tracking mode with DAO likewise activated. Then, beginning at step 304, the microcontroller monitors heart rhythm and paces the heart in accordance with the current AMS mode (initially tracking) while performing DAO pacing. At step 306, the microcontroller determines the current FARI interval based only on atrial-sensed events using FARI-based AF detection unit 152 (FIG. 3). This is in contrast with conventional FARI-based techniques, which typically count both atrial-sensed and atrial-paced events.

Then, if the AMS system is currently in the tracking mode and the FARI value exceeds a predetermined threshold (the ATDR threshold), the AMS system automatically switches to the non-tracking mode, at step 308, and DAO is deactivated, at step 310. If the FARI remains below the ATDR threshold while in the tracking mode, processing simply returns directly to step 304 for further monitoring of pacing in the non-tracking mode with DAO. Alternatively, if the AMS system has already been switched to the non-tracking mode and the FARI value falls below the ATDR threshold, the AMS system automatically switches back to the tracking mode, at step 312, and DAO is reactivated, at step 314. If the FARI value remains above the ATDR threshold while in the non-tracking mode, processing also returns directly to step 304 for further monitoring of the heart rhythm and selective pacing (without DAO).

Figure 5:
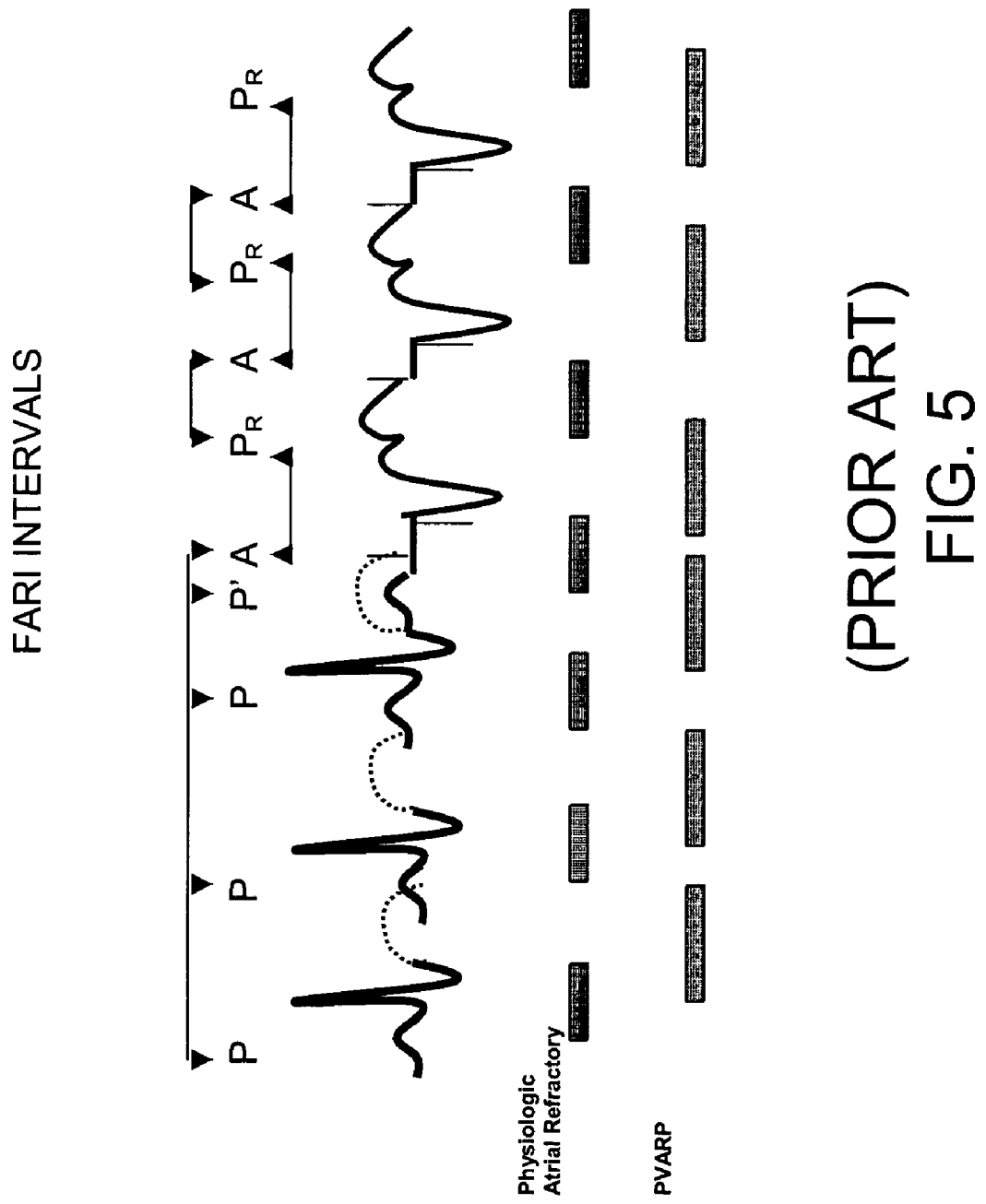
FIG. 5 is a timing diagram illustrating intervals used in conjunction with conventional FARI techniques.
Figure 6:
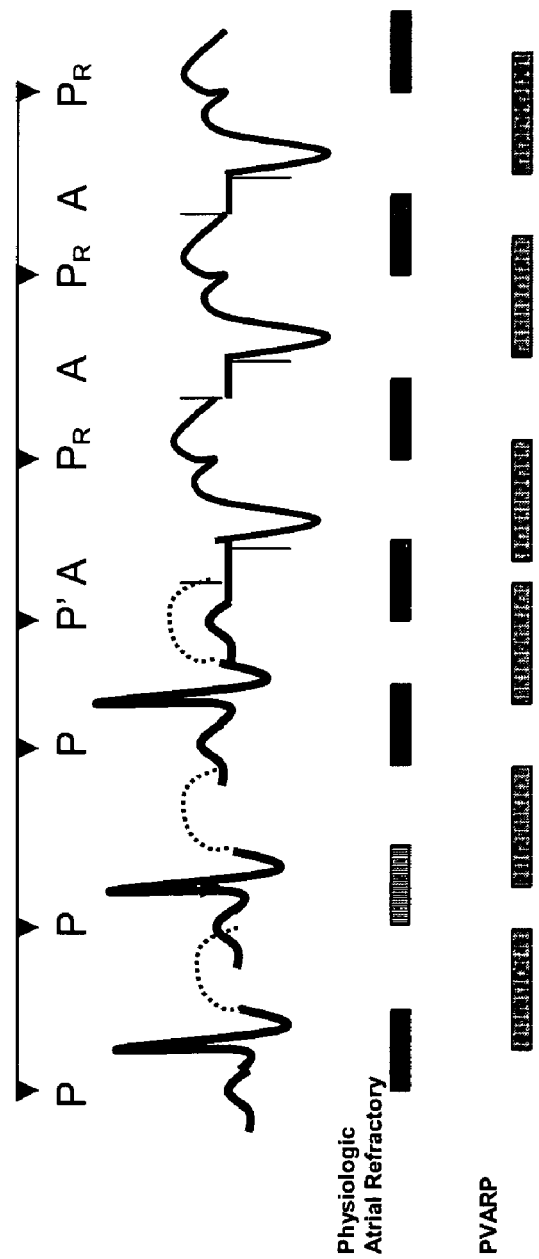
FIG. 6 is a timing diagram illustrating intervals used in conjunction with the improved FARI technique of FIG. 4.

Intervals used for FARI calculation are shown in FIGS. 5 and 6. More specifically, FIG. 5 illustrates conventional FARI intervals and FIG. 6 illustrates the intervals used in connection with the improved technique of FIG. 4. Within both figures, schematic representation of the physiological atrial refractory intervals and PVARP intervals are shown along with an exemplary atrial surface electrocardiogram (EKG). P represents a P-wave that is tracked; P' represents an atrial premature beat that coincides with a PVARP and is not tracked; PR represents a retrograde P-wave that coincides with PVARP and hence is also not tracked; and A represents a paced atrial event. T waves are shown within the EKG in dotted lines so as not to obscure the P-waves. Arrows identify the start and end of each atrial interval used in the calculation of FARI.

With conventional FARI techniques, all atrial events, whether paced or sensed, are used to calculate FARI. In FIG. 5, arrows are provided along with each atrial event used in the calculation of FARI. As explained above, circumstances can arise (such as RNRVAS) when the atrial rate based on FARI is significantly different from the actual atrial rate because the calculation of the FARI includes all paced events, even those that occur during periods in which the atria is physiologically refractory. In FIG. 5, for example, the last atrial-paced event shown therein occurs during an interval when the atria are physiologically refractory. When the atria are physiologically refractory, the paced events do not capture and do not affect the actual atrial rate. However, since the FARI algorithm uses all atrial events (both paced as well as sensed) in the determination of the atrial rate, the resulting calculated atrial rate may be incorrect. FIG. 6, in contrast, shows the intervals used in connection with the improved technique of FIG. 4. Only sensed atrial events are used to calculate the FARI and so FARI arrows only appear next to sensed events. By ignoring the atrial-paced events, the FARI will never inappropriately exceed the ATDR and a mode switch will not occur even in circumstances such as RNRVAS.

Thus, FIG. 4 provides an overview of a technique whereby the FARI value is calculated the based upon atrial-sensed events only. The technique of FIG. 4 is preferably employed in DAO implementations that do not include an atrial capture verification system. If atrial capture verification is provided, the system can distinguish between paced events that capture and those that do not for the purposes of FARI calculation.

Figure 7:
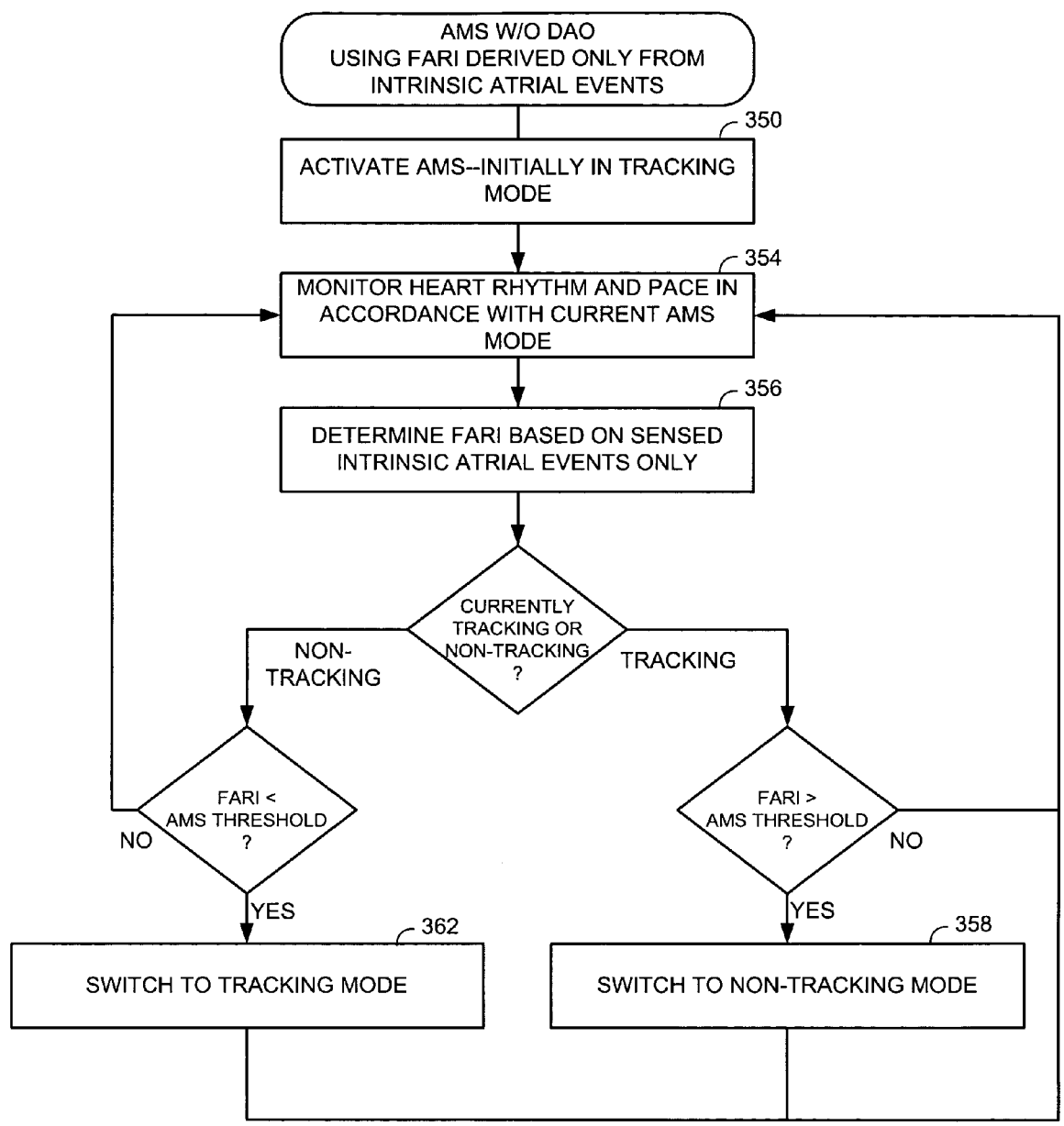
FIG. 7 is a flow chart illustrating the manner by which the microcontroller of FIG. 2 controls the FARI system to calculate a FARI value using only atrial-sensed events so as to reduce risk of inappropriate mode switching by the AMS system caused by RNRVAS arising absent DAO.
Figure 8:
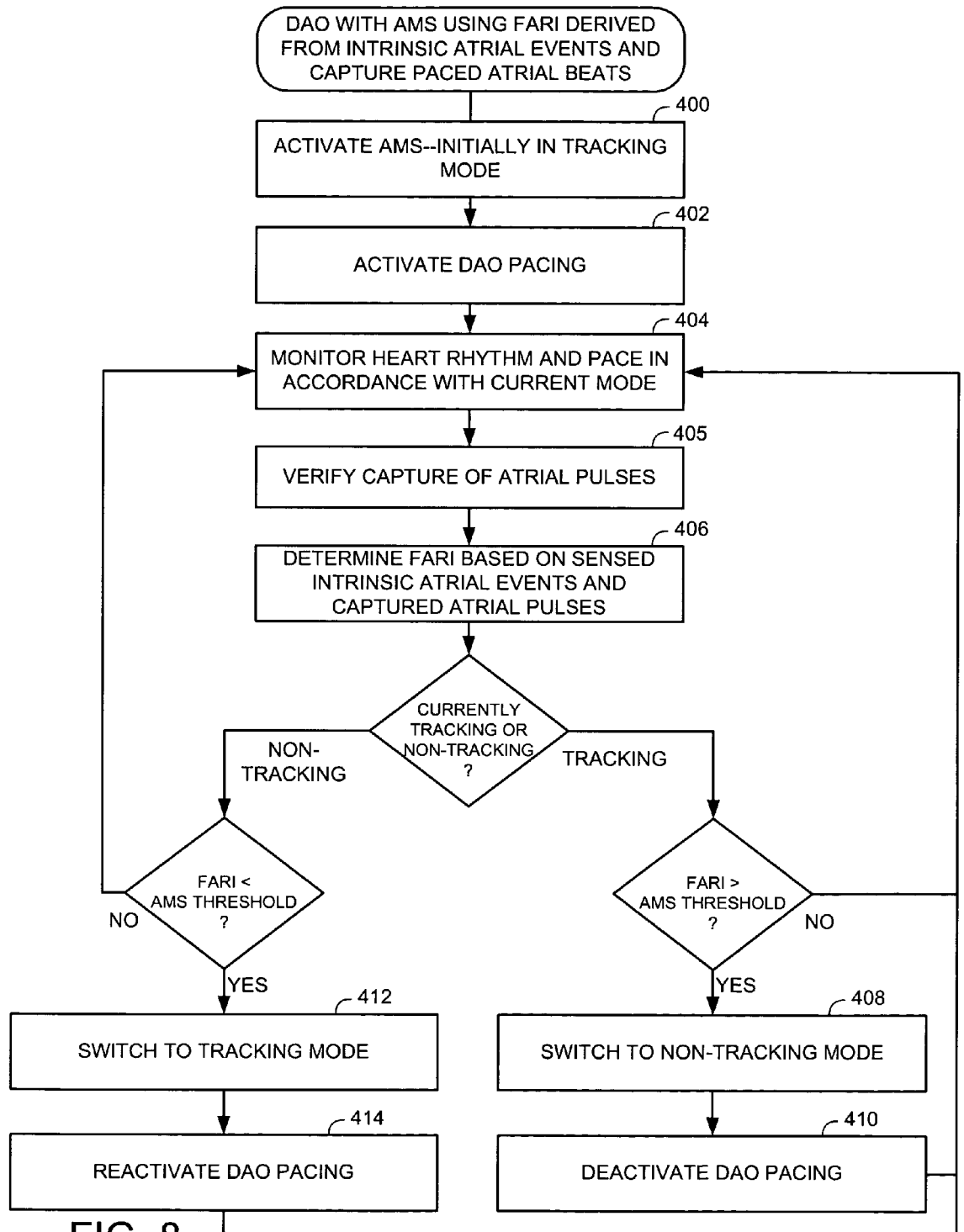
FIG. 8 is a flow chart illustrating the manner by which the microcontroller of FIG. 2 controls the FARI system during DAO to calculate a FARI value using atrial-sensed events and captured atrial events to reduce risk of inappropriate mode switching during DAO.
Figure 9:
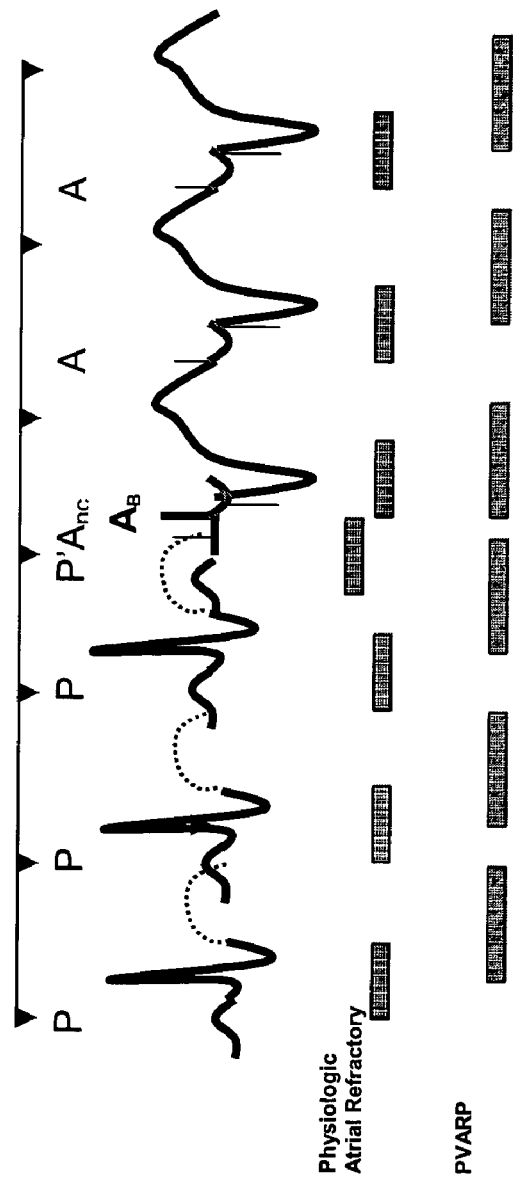
FIG. 9 is a timing diagram illustrating intervals used in conjunction with the improved capture-based FARI technique of FIG. 8.
Figure 10:
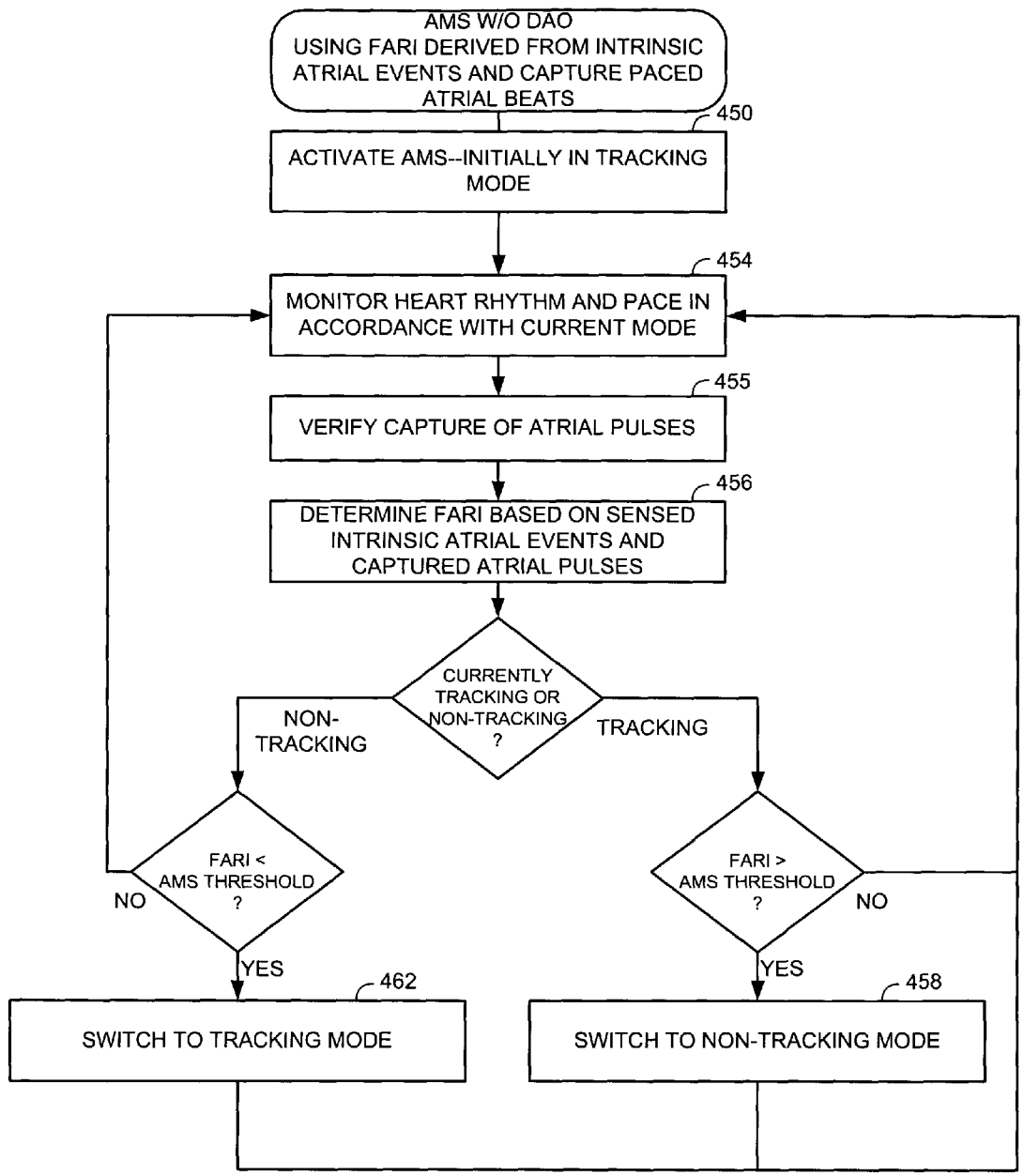
FIG. 10 is a flow chart illustrating the manner by which the microcontroller of FIG. 2 controls the FARI system to calculate a FARI value using atrial-sensed events and captured atrial events to reduce risk of inappropriate mode switching arising absent DAO.

The technique of FIG. 4 need not be implemented in conjunction with DAO. This is illustrated in FIG. 7. Briefly, the microcontroller activates AMS, at step 350, then begins pacing the heart in the tracking mode, at step 354. At step 356, the current FARI interval is the calculated based on atrial-sensed events only. As before, if the AMS system is currently in the tracking mode and the FARI value exceeds the ATDR threshold, the AMS system automatically switches to the non-tracking mode, at step 358. If the AMS system has already been switched to the non-tracking mode and the FARI value falls below the ATDR threshold, the AMS system automatically switches back to the tracking mode, at step 362. As before, by excluding atrial-paced events, inappropriate mode switch is avoided, particularly in the case of RNRVAS. FIGS. 8–10 illustrate techniques for use if atrial capture verification is available. Many of the steps of the techniques of FIGS. 8–10 are similar or identical to those of FIGS. 4–7 and only pertinent differences will be described in detail. FIG. 8 illustrates a DAO implementation. As with the DAO technique of FIG. 4, the microcontroller activates AMS and DAO, at steps 400 and 402, then begins pacing the heart in the tracking mode while performing DAO pacing, at step 404. At step 405, the atrial capture verification system (FIG. 3) is employed to verify capture of each atrial pacing pulse and, if any pulse is not captured, a backup pulse is delivered. At step 406, the microcontroller then determines the current FARI interval based on a combination of atrial-sensed events and captured atrial-paced events, again using the FARI-based AF detection unit (FIG. 3). This is in contrast with both the conventional FARI-based techniques (wherein both atrial-sensed and atrial-paced events and counted) and the technique of FIG. 4 (wherein only atrial-sensed events are counted).

As before, if the AMS system is currently in the tracking mode and the FARI value exceeds the ATDR threshold, the AMS system automatically switches to the non-tracking mode, at step 408, and DAO is deactivated, at step 410. If the AMS system has already been switched to the non-tracking mode and the FARI value falls below the ATDR threshold, the AMS system automatically switches back to the tracking mode, at step 412, and DAO is reactivated, at step 414. By excluding non-captured atrial-paced events, inappropriate mode switch during DAO is likewise avoided. Note that the specific value for the ATDR threshold used with the technique of FIG. 4 may differ from the threshold used with the technique of FIG. 8.

Intervals used for FARI calculation using the technique of FIG. 8 are shown in FIG. 9. P represents a P-wave that is tracked; P' represents an atrial premature beat that coincides with a PVARP and is not tracked; A represents a paced atrial event; $A_{nc}$ represents an atrial output pulse that does not capture; and $A_B$ represents atrial back up pulse. In the example of FIG. 9, $A_{nc}$ pulse failed to capture because it was delivered while the atria was physiologically refractory as a result of a preceding atrial premature beat. T waves are again shown in dotted lines so as not to obscure the P-waves. Arrows identify the start and end of each FARI.

With atrial capture verification enabled, the atrial back-up pulse following $A_{nc}$ is likely to capture unless it is also too close to the preceding P' complex. If it captures, even though optimal AV synchrony may be lost for that one cycle, it will prevent retrograde conduction and hence, prevent both RNRVAS and the cascade of subsequent events described above in the Summary that result in the calculated atrial rate then being twice the actual rate. In any case, by calculating FARI based on atrial-sensed events and those paced events that actually capture in accordance with the technique of FIG. 8, the atrial rate calculated based on FARI is likely to be a more accurate indication of the actual atrial rate and inappropriate mode switching is avoided.

FIG. 10 illustrates a non-DAO version of FIG. 8. Briefly, the microcontroller activates AMS, at step 450, then begins pacing the heart in the tracking mode, at step 454. At step 455, capture of each atrial pacing pulse is verified and, if any pulse is not captured, a backup pulse is delivered. At step 456, the current FARI interval is calculated based on a combination of atrial-sensed events and captured atrial-paced events. As before, if the AMS system is currently in the tracking mode and the FARI value exceeds the ATDR threshold, the AMS system automatically switches to the non-tracking mode, at step 458. If the AMS system has already been switched to the non-tracking mode and the FARI value falls below the ATDR threshold, the AMS system automatically switches back to the tracking mode, at step 462. As before, by excluding all non-captured atrial-paced events, inappropriate mode switch is avoided particularly in circumstance of RNRVAS.

AF Detection Techniques a. Capture-Based AF Detection

With reference to the remaining figures, various techniques for detecting the onset of AF or other atrial tachycardias will be described. The techniques are advantageously used in connection with AMS to prevent inappropriate mode switching but may be used in other circumstances as well. When used with AMS, the techniques also preferably employ the improved FARI calculation techniques described above.

Figure 11:
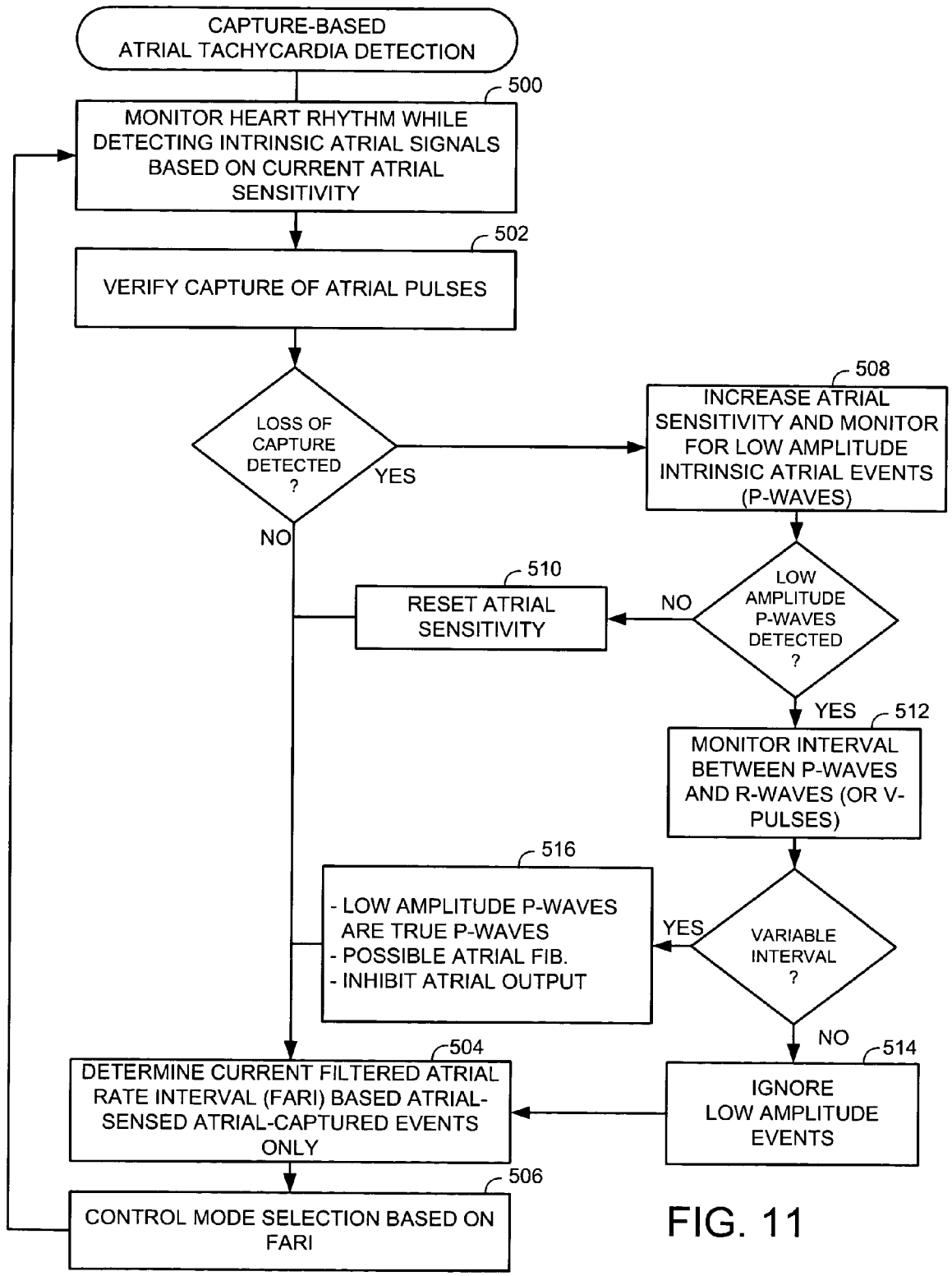
FIG. 11 is a flow chart illustrating the manner by which the microcontroller of FIG. 2 controls the AF detection system of FIG. 3 to detect AF following detection of an atrial loss of capture while in a tracking mode.
Figure 12:
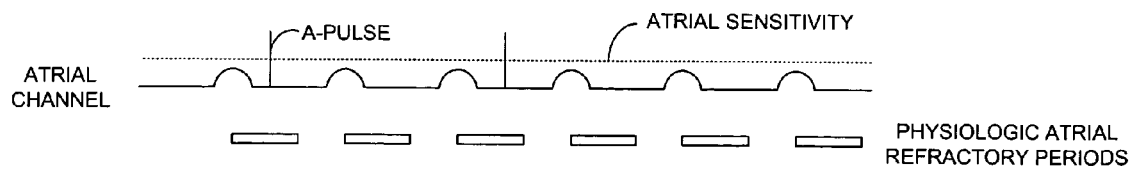
FIG. 12 is a timing diagram illustrating low amplitude P-waves to be detected using sensitivity adjustment in accordance with the capture-based technique of FIG. 11.

Referring first to FIGS. 11–14, a capture-based AF detection technique will now be described. Briefly, loss of capture of an atrial pacing pulse is used to trigger a search for low-amplitude P-waves that might be indicative of an ongoing, but as yet undetected, atrial tachycardia. More specifically, the loss of capture of the atrial pacing pulse might have occurred because the atria was refractory at the time the pulse was delivered as a result of a previous intrinsic P-waves that had sufficient voltage to depolarized atrial yet was not sufficiently strong to be detected by the implanted device. This is illustrated in FIG. 12, which shows a series of P-waves below a detection threshold as well as two A-pulses delivered during physiological atrial refractory periods and therefore not captured.

Figure 13:
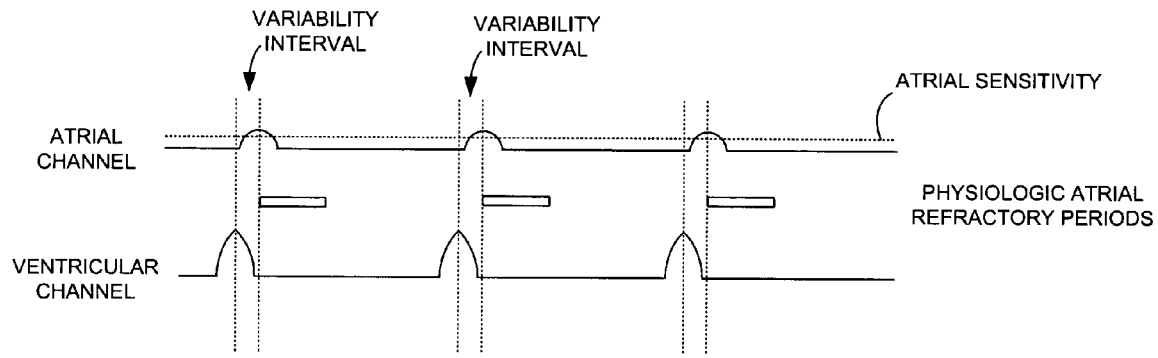
FIG. 13 is a timing diagram illustrating low amplitude P-waves detected using the capture-based technique of FIG. 11, which are actually far-field R-waves.
Figure 14:
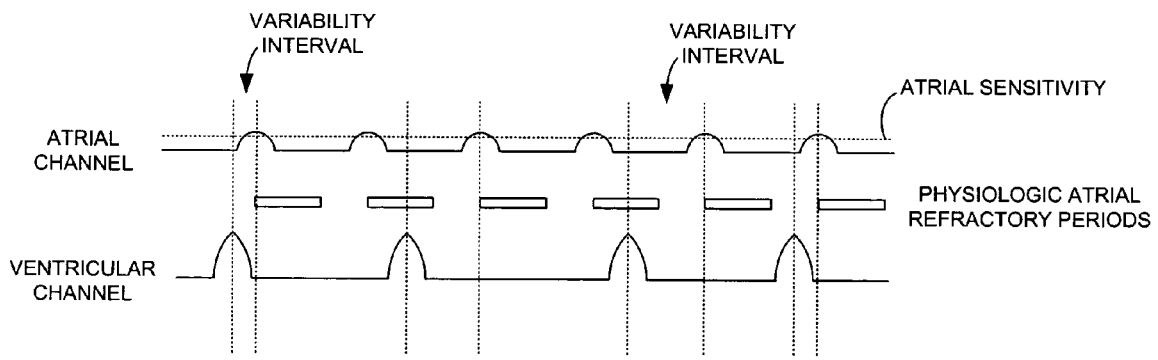
FIG. 14 is a timing diagram illustrating low amplitude P-waves detected using the capture-based technique of FIG. 11, which are true P-waves indicative of atrial tachycardia.

Thus, loss of capture of the atrial pacing pulse may be indicative of an atrial tachycardia represented primarily by intrinsic P-waves not sufficiently strong to be detected. Accordingly, the AF detection system automatically changes the sensitivity by which atrial events are detected so as to detect low-amplitude P-waves. If such low-amplitude P-waves are detected, the system then verifies that the P-waves are true P-waves based on a degree of variability between P-waves and ventricular events (as detected on a separate ventricular channel). In FIG. 13, a "variability interval" between P-waves and R-waves remains constant and within a specified window (not specifically shown), indicating that the P-waves are probably far-field versions of the R-waves. The window is used to rule out retrograde P-waves that will occur later than FFRWs. Also retrograde P-waves can be associated with loss of capture but there will be no other P-waves whereas FFRW will occur earlier and will never be associated with loss of capture, as these are not true atrial depolarizations. There can be situations where Pr complexes result in functional loss of atrial capture but, when the sensitivity is increased, FFRWs are also detected. True retrograde P-waves and FFRWs are both stable with respect to a preceding QRS complex but the intervals between these two detected atrial signals will differ from one another and so the interval can be used to distinguish there-between. In FIG. 14, the variability intervals between P-waves and R-waves are not constant indicating that the P-waves are probably true P-waves associated with true atrial tachyarrhythmias such as atrial fibrillation. If the low-amplitude P-waves are determined to be true intrinsic atrial events (as in FIG. 14), then these events are thereafter used to update of the FARI value for use in detecting the presence of atrial tachycardia and for controlling mode switching.

The loss of capture-based AF detection technique will now be described in the greater detail with reference to the specific steps of FIG. 11. Initially, at step 500, capture-based AF detection unit 154 of AF detection system 105 of FIG. 3 inputs electrical cardiac signals, detects intrinsic atrial events with an atrial channel of the cardiac signals, and delivers any necessary atrial pacing pulses. DAO may be simultaneously performed. Atrial events are detected based on an initial atrial sensitivity level. Events that do not exceed a threshold level set based upon the atrial sensitivity are thereby not detected. (Note that the higher the atrial sensitivity, the lower the threshold for detection. Hence, an increase in sensitivity permits lower-amplitude events to be detected.) At step 502, the system verifies capture of atrial pulses using capture verification system 107 of FIG. 2. Assuming no loss of capture is detected, the system then updates the FARI value based upon detected atrial-sensed events and captured atrial-paced events, at step 504, and then controls mode selection based upon the FARI value, at step 506. As discussed above, if the FARI value exceeds a predetermined threshold, the system switches from the tracking mode to the non-tracking mode using AMS system 101 of FIG. 2. So long as there is no loss of capture of atrial pulses, steps 500–506 are performed continuously in a loop.

However, once a loss of capture is detected, the system instead performs a sequence of steps to determine whether the loss of capture is a result of an ongoing atrial tachycardia that has not yet been detected because the P-waves arising during the tachycardia are below the P-wave detection threshold. To this end, at step 508, the system increases the atrial sensitivity and monitors newly received atrial signals to detect low amplitude P-waves. If no low amplitude P-waves are detected, indicating that the previous loss of capture arose for reasons other than an ongoing atrial tachycardia, then the atrial sensitivity is reset at step 510 and processing continues at step 504. If low amplitude P-waves are detected, the system then takes steps to verify that the low amplitude P-waves are not merely far-field R-waves or other far-field ventricular events. More specifically, at step 512, the system detects the interval between the P-waves and R-waves-V-pulses detected on a separate ventricular channel. If there is no variation in the interval between the P-waves and the R-waves/V-pulses, i.e. the interval therebetween is substantially fixed, then the low amplitude P-waves are ignored, at step 514. As noted, such low amplitude events are either retrograde atrial events occurring in the absence of a true tachycardia or FFRWs. An examination of the coupling interval can be used to distinguish therebetween, if desired. Such FFRWs would not be the cause of the original loss of capture detected at step 502 but would instead just be the result of the increased atrial sensitivity.

Processing continues at step 504 for updating the FARI interval based only on true P-waves. On the other hand, if the interval between the low-amplitude P-waves and the ventricular events has a sufficiently high degree of variability, then the low amplitude P-waves are classified as true P-waves at step 516. Since a possible atrial tachycardia is occurring, atrial outputs are inhibited. Processing continues at step 504 where the system updates the FARI value while incorporating the true low-amplitude P-waves and, if the updated FARI value exceeds the mode switching threshold, the system thereby detects the atrial tachycardia and automatically switches from the tracking to the non-tracking mode, at step 506. The implanted device remains in the non-tracking mode until the FARI value falls below the threshold and the device then switches back to the tracking mode.

In this manner, the degree of variability between the low attitude P-waves and R-waves/V-pulses is used as a basis to distinguish between true and false P-waves to aid in the detection of true atrial tachycardia. The degree of variability in the interval between P-waves and R-waves/V-pulses is detected using otherwise conventional techniques and is then compared with a predetermined threshold indicative of the degree of variability expected to arise between true P-waves and R-waves/V-pulses. Briefly, if the low amplitude P-waves are actually far-field R-waves, then the interval between events detected within the atria and the ventricles will be a substantially fixed interval of time. (Note that, if the interval is stable, the actual length of the interval will depend on whether the detected signal is retrograde or FFRW with a shorter interval suggestive of FFRW and a longer interval consistent with retrograde P (Pr). Accordingly, an examination of the length of the interval can help distinguish between these two cases.) On the other hand, if the low amplitude P-waves are true P-waves, then the generally chaotic nature of the heart ensures some degree of natural variability during an atrial fibrillation. When it is an organized atrial tachycardia apropos of atrial flutter, the interval may be stable. See U.S. patent application Ser. No. 10/367,327, filed Feb. 13, 2003, entitled "Method and Apparatus for Detecting and Managing Atrial Flutter", which is incorporated herein by reference.

In any case, the actual threshold value used to evaluate the degree of variability may be determined experimentally using otherwise routine techniques. For information regarding techniques for evaluating a degree of randomness within heart rate, see U.S. patent application Ser. No. 10/017,836, entitled "Dynamic Control Of Overdrive Pacing Based On Degree Of Randomness Within Heart Rate", of Kroll et al., filed Dec. 12, 2001, which is incorporated by reference herein. See also U.S. Pat. No. 5,350,401 to Levine, which is also incorporated herein by reference. With that technique, upon detection of loss of capture of a ventricular pulse, the ventricular pulse output magnitude is increased and another pulse is delivered. If that pulse also fails to capture, the output magnitude is increased again. This process proceeds until either a ventricular pulse captures or until a maximum pulse output level is reached. If the maximum output is reached and the ventricular pulses still do not evoke capture, a determination is thereby made that a low amplitude ventricular fibrillation (VF) may have occurred and a defibrillation shock may then be delivered to terminate the VF.

b. Alternating Event-Based AF Detection

Figure 15:
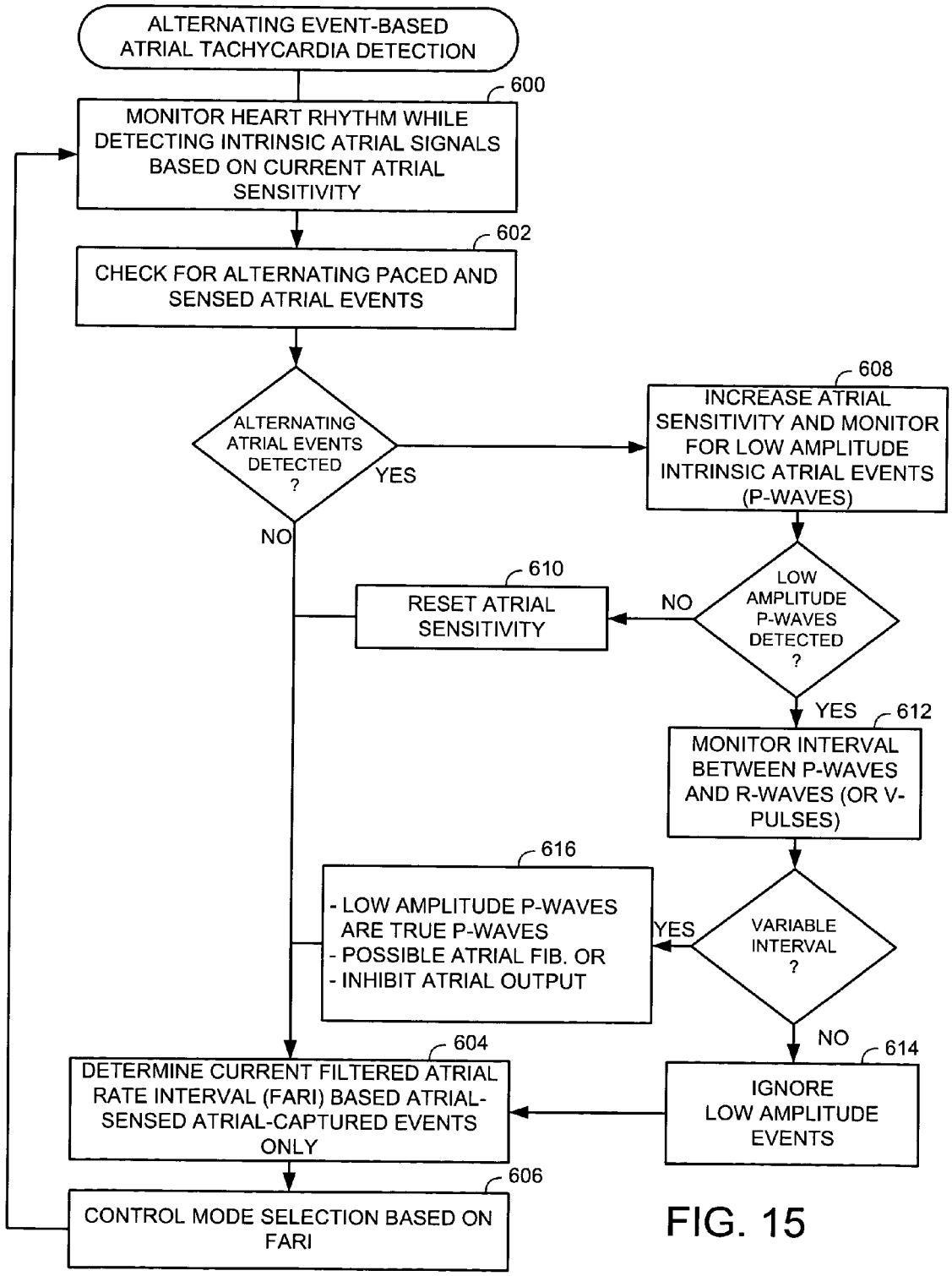
FIG. 15 is a flow chart illustrating the manner by which the microcontroller of FIG. 2 controls the AF detection system of FIG. 3 to detect AF following detection of alternating atrial-paced and atrial-sensed events while in the tracking mode.

Referring now to FIG. 15, an alternating event-based AF detection technique will be described. The technique is similar to the capture-based technique of FIG. 11 but a sequence of alternating paced and sensed atrial events is instead used to trigger the search for low-amplitude P-waves that might be indicative of an ongoing atrial tachycardia. Alternatively, the sequence of alternating paced and sensed atrial events might have occurred due to RNRVAS, which can result in an alternating pattern of A-pulses and retrograde P-waves. As before, the AF detection system automatically changes the sensitivity by which atrial events are detected so as to detect low-amplitude P-waves and verifies that any low-amplitude P-waves are true P-waves based on a degree of variability. If the low-amplitude P-waves are deemed to be true intrinsic atrial events, then these events are used to update of the FARI value for use in detecting the atrial tachycardia and for controlling mode switching.

The alternating event-based AF detection technique will now be summarized with reference to the steps of FIG. 15. As this technique is similar to the technique of FIG. 11, only pertinent differences will be described in detail. At step 600, alternating pace/sensed event AF detection unit 156 of FIG. 3 inputs electrical cardiac signals, detects intrinsic atrial events, and delivers any necessary atrial pacing pulses. At step 602, the system monitors the atrial events to detect an alternating sequence of paced and sensed atrial events, i.e. A-pulse-P-wave-A-pulse-P-wave-A-pulse-P-wave and so on. To this end, the system counts the number of pairs of events that arise in such as alternating sequence and, if the number exceeds some predetermined threshold, then the device performs steps to determine whether the alternating sequence is a result of an ongoing atrial tachycardia that has not yet been detected. As before, at step 608, the system increases the atrial sensitivity to detect low amplitude P-waves. If no low amplitude P-waves are detected, indicating that the alternating sequence of paced and sensed events arose for reasons other than an ongoing atrial tachycardia, then the atrial sensitivity is reset at step 610 and processing continues at steps 604 and 606 to update the FARI and perform any needed mode switching. If low amplitude P-waves are detected, however, the system evaluates the degree of variability between atrial and ventricular events at step 612. If the degree of variability is sufficiently high, the low amplitude P-waves are classified as true P-waves with possible AF at step 616 and processing then continues at step 604 where the P-waves are taken into account in updating the FARI value. If it now exceeds the AF threshold, AF is thereby detected and a mode switch to the non-tracking mode is performed at step 606. If, however, the degree of variability is not sufficiently high when evaluated at step 612, the low amplitude events are ignored, at step 614.

Thus, a sequence of alternating paced and sensed atrial events is used to trigger a procedure for detecting a possible ongoing atrial tachycardia that has not yet been detected. The number of pairs of alternating events needed to trigger the procedure may be set, for example, to a value in the range of 10–20. Other numerical values may be determined experimentally using otherwise routine techniques.

Note that the alternating pattern of events may also be due to atrial bigeminy with APCs. Atrial bigeminy is a supraventricular rhythm wherein an atrial extrasystole follows every sinus beat. It is rare, however, for the APCs to occur so early as to coincide with the PVARP unless the PVARP is very long. As such, they are likely to be detected if the atrial sensitivity is appropriate. If the APC is significantly smaller than the sinus beat, the APC may be subthreshold with respect to detection allowing delivery of an atrial output, which will demonstrate functional loss of capture as it coincided with the physiological refractory period. But in this situation, the system will detect loss of capture but not an atrial tachyarrhythmia as the APC is not sensed. When the sensitivity is increased, the APC will be detected but in accord with the foregoing technique, an atrial output will be withheld or the atrial output will not be counted and the system will not recognize a tachycardia.

c. Pattern-Based AF Detection

Figure 16:
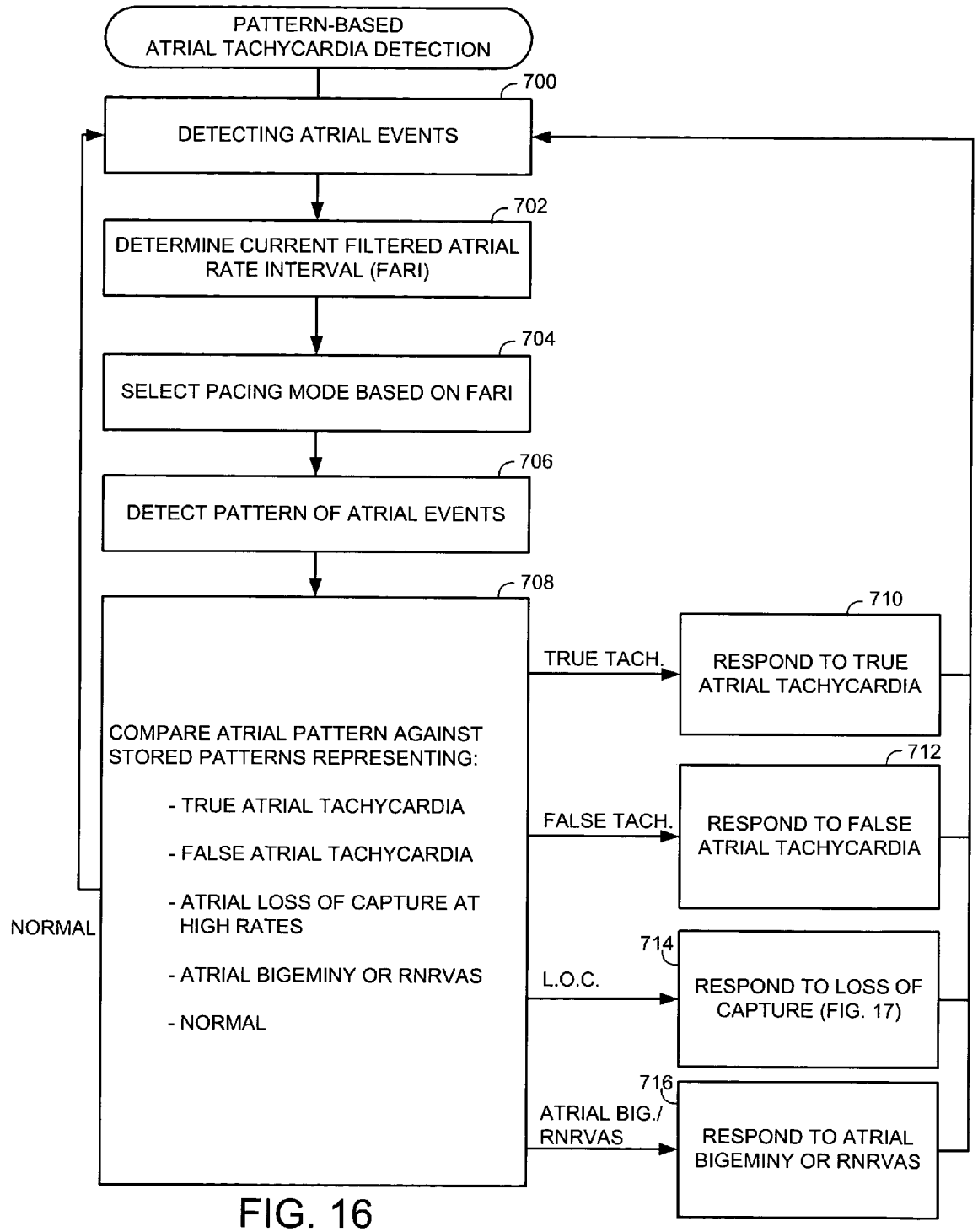
FIG. 16 is a flow chart illustrating the manner by which the microcontroller of FIG. 2 controls the AF detection system of FIG. 3 to detect AF following detection of selected patterns of atrial events while in the tracking mode.

Whereas the foregoing technique operates to detect one particular pattern of atrial events, namely a sequence of alternating paced and sensed events, the technique of FIG. 16 operates to detect any of a wide variety atrial event patterns for comparison against stored patterns representative of various normal or abnormal rhythms.

Initially, at step 700, the device detects atrial events using a current atrial sensitivity level. At step 702, the device determines the FARI either based on atrial-sensed events only or, if atrial auto-capture is available, based on both atrial-sensed and captured atrial-paced events. In any case, at step 704, the device selects the current AMS pacing mode based on the atrial rate as derived from the FARI in comparison with an ATDR. Then, at step 706, the device detects the current pattern of atrial events so that it may be compared against stored patterns representative of certain rhythms. More specifically, at step 708, the device compares the current pattern of atrial events against stored patterns representing, e.g.:

1) true atrial tachycardia;
2) false atrial tachycardia;
3) loss of capture at high atrial rates;
4) atrial bigeminy or RNRVAS; or
5) normal rhythm.

Then, if a true atrial tachycardia is detected based upon the pattern of events, step 710 is performed wherein the device responds to the atrial tachycardia. For example, if currently in a tracking mode, the device switches to non-tracking mode. If already in the non-tracking mode, the device may increase the atrial sensitivity in effort to detect any underlying low-amplitude atrial tachycardia events as described above in connection with FIG. 15. If, however, the pattern events is indicative of a false atrial tachycardia then step 712 is performed wherein the device responds to the false tachycardia. For example, if currently in the non-tracking mode, the device switches back to the tracking mode to thereby ignore the false tachycardia. The atrial sensitivity may also be adjusted to avoid detection of additional false tachycardias. Diagnostic information may be recorded pertaining to the false tachycardia. If already tracking, then, typically, no steps are taken other than to record diagnostic information pertaining to the false tachycardia.

If the latest atrial pattern is indicative of atrial loss of capture at high atrial rates, then step 714 is performed wherein the device responds to the loss of capture. In one example, the atrial pulse magnitude is increased in effort to ensure capture. (Note, that if the device is capable of directly detecting atrial loss of capture, then this step need not be performed since loss of capture will be directly detected and the atrial pulse amplitude increased without the need for examining the pattern of atrial events.) If the increase in output is unsuccessful in restoring atrial capture, the device may then decrease the atrial rate. Preferably, however, the device selectively decreases the atrial rate before it increases the atrial output so as to allow more time for the atrial physiologic refractory period to recover to thereby avoid loss of capture due to physiologic refractoriness. In this regard, if there is functional loss of capture due to a true atrial event in the PVARP rendering the atrial myocardium physiologically refractory, the atrial output will not capture—no matter how high the output. Thus, increasing the atrial output is not likely to be helpful in this situation although increasing the atrial output will correct a true loss of capture state when and if the myocardium is physiologically capable of being depolarized at that point in the cycle. However, slowing the atrial rate will allow time for the atrial myocardium to recover on a physiologic basis and even without an increase in the atrial output, capture is likely to be restored. Note that certain predecessor devices of Pacesetter, Inc. provided a feature wherein the rate is effectively slowed after a PVC so that any atrial output will thereby be effective and not coincide with the physiologically refractory period initiated by a retrograde P-wave. The choice of response at step 714 to atrial loss of capture depends upon the atrial rate at the time the events are recognized. If faster than a preset rate, the atrial rate is slowed before the output is increased. Otherwise, the output is increased immediately. In either case, the response will not prevent a couple of potential cycles and of this rhythm from occurring but will prevent the rhythm from becoming sustained.

Figure 17:
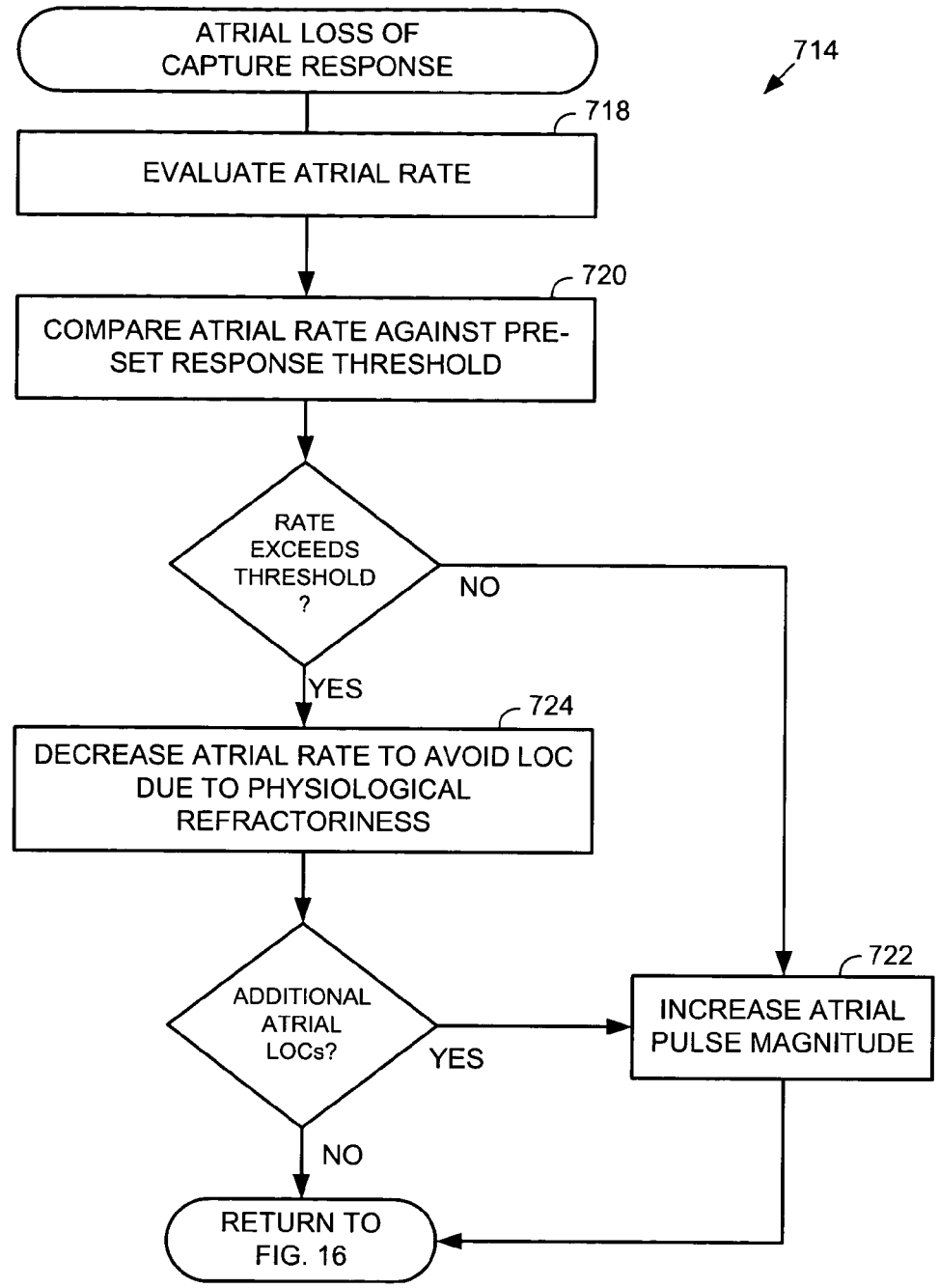
FIG. 17 is a flow chart illustrating steps performed in response to the detection of an atrial loss of capture using the technique of FIG. 16.

The processing of step 714 is summarized by FIG. 17. Briefly, at step 718, the atrial rate is evaluated and then compared, at step 720, against a pre-set rate threshold at step 720. If the atrial rate is below the rate threshold, the atrial pulse magnitude is immediately increased at step 722 to avoid further loss of capture due to insufficient pulse magnitude. If, instead, the atrial rate exceeds the rate threshold, the atrial rate is decreased at step 724 to avoid further loss of capture due to physiological refractoriness. If atrial loss of capture continues, then the pulse magnitude is also increased at step 722. If, however, the decrease is atrial rate in sufficient to prevent further atrial loss of capture, then an increase in pulse magnitude is not required. In any case, processing ultimately returns to FIG. 17 for continued monitoring of event patterns. Appropriate values for the pre-set rate threshold may be determined experimentally. Typically, though, the rate threshold is set to a value between the programmed base rate and the maximum sensor rate, commonly between 60 to 120 beats per minute (bpm).

If an atrial bigeminy or RNRVAS is detected based upon the pattern events, then step 716 is performed wherein the device responds to the atrial bigeminy or RNRVAS. For example, steps may be taken to determine whether the rhythm is due to RNRVAS or due to atrial bigeminy with appropriate steps then taken. Slowing of the atrial rate will restore capture and terminate RNRVAS where as slowing of the atrial rate will not necessarily terminate frequent APCs and the bigeminal pattern will persist. In any case, thereafter processing returns to step 700 for detection of additional atrial events so that the most recent pattern of events may be updated for review at step 708. Also, if the pattern does not match any of the abnormal patterns of step 708, then a normal rhythm is thereby identified and processing returns directly to step 700.

TABLE I illustrates exemplary sequences of atrial events and corresponding heart rhythms for comparison at step 708, wherein a sequence of four events is used to form the pattern.

TABLE I

| PATTERN DESIGNATOR | ATRIAL EVENT PATTERN | POSSIBLE CAUSE |
|---|---|---|
| 0 | PPPP | Zero Pacing (All Events Are Sensed) |
| 1 | PPPA | Normal Rhythm |
| 2 | PPAP | Normal Rhythm |
| 3 | PPAA | Normal Rhythm |
| 4 | PAPP | Normal Rhythm |
| 5 | PAPA | Atrial Bigeminy with APCs or RNRVAS (with Alternating Retrograde P-waves) |
| 6 | PAAP | False Atrial Tachycardia or Loss Of Capture At High Rates |
| 7 | PAAA | Loss Of Capture at High Rates (1 in 3) |
| 8 | APPP | Normal Rhythm |
| 9 | APPA | False Atrial Tachycardia |
| 10 | APAP | Atrial Bigeminy with APCs or RNRVAS |
| 11 | APAA | Loss Of Capture at High Rates or APCs |
| 12 | AAPP | Normal Rhythm |
| 13 | AAPA | Loss Of Capture At High Rates (1 in 4) |
| 14 | AAAP | Loss Of Capture At High Rates (1 in 4) |
| 15 | AAAA | 100% Atrial Pacing--Possible Atrial Undersensing |

Note that patterns 1, 2, 4 and 8 are the same rhythm caught at different times in the sequence. Likewise, patterns 3 and 12 are the same, patterns 5 and 10 are the same, and patterns 7, 13 and 14 are the same. Also, note that loss of capture at high rates (patterns 7, 13 and 14) is consistent with either a true atrial tachycardia or RNRVAS or its equivalent. Accordingly, to distinguish a true tachycardia with low amplitude signals from functional loss of capture associated with single true P-waves (whether APC or retrograde as with RNRVAS), the device either increases the atrial sensitivity to detect additional P-waves or adjusts the rate or atrial pulse output magnitude in accordance with the various techniques already described.

Thus, TABLE I provides a pattern-matching example wherein each pattern includes four atrial events. In general, however, other numbers of events may be examined against pre-determined patterns indicative of the various rhythms. For example, patterns containing five or six events or more can be stored for comparison against on-going patterns. Also, the device preferably does not compare each sequence of events against the stored patterns. Rather, the device seeks to first identify sustained patterns. In one example, the device maintains a running average of ongoing patterns to identify a sustained pattern or to at least determine which pattern occurs most frequently. Then, only sustained patterns (or patterns that occur most frequently) are compared against the stored patterns. As can be appreciated, a wide variety of implementations may be provided in accordance with the general pattern-matching principles of the invention.

d. AF Verification in Non-Tracking Mode

Figure 18:
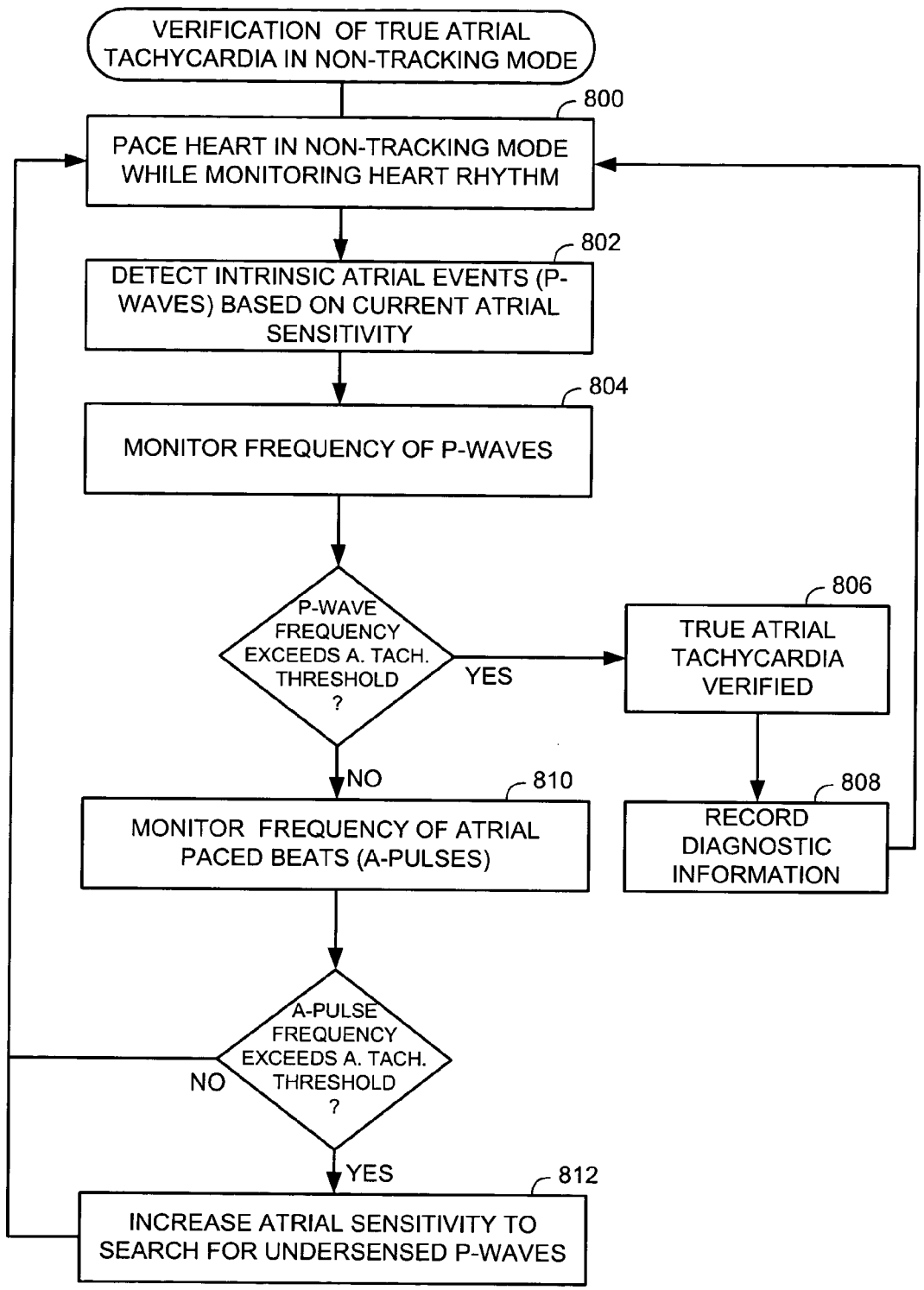
FIG. 18 is a flow chart illustrating the manner by which the microcontroller of FIG. 2 controls the AF detection system of FIG. 3 to verify the onset of a true atrial tachycardia while in a non-tracking mode.

FIG. 18 provides a technique for determining whether an actual atrial tachycardia is on going while an AMS pacing device is in a non-tracking mode. Since the device is already non-tracking, no mode switching need be performed upon detection of the atrial tachycardia. However, such information is useful for diagnostic purposes and so the technique of FIG. 18 operates to identify AF while in a non-tracking mode and to store diagnostic data in memory for subsequent transmission to an external programmer for review by a physician.

Initially, at step 800, the heart is paced in the non-tracking mode while the heart rhythm is monitored. At step 802, intrinsic atrial events, such as P-waves, are detected based upon the current atrial sensitivity. At step 804, the frequency of intrinsic atrial events is monitored. If this frequency exceeds an atrial-sensed event threshold, the device thereby concludes, at step 806, that a true atrial tachycardia has occurred and appropriate diagnostic information is stored, at step 808, for subsequent review by the physician. On the other hand, if the frequency does not exceed the atrial-sensed beat threshold, then step 810 is instead performed wherein the device monitors the frequency of A-pulses. If the frequency of A-pulses exceeds the atrial-paced event threshold, then step 812 is performed wherein the atrial sensitivity is increased to search for under-sensed P-waves, i.e. P-waves with low-amplitudes. Processing then returns through step 800 to step 804 wherein the device again examines the frequency of P-waves. Since the sensitivity has been increased, any undersensed P-waves should now be detected and, if an atrial tachycardia is occurring, the P-wave frequency should now exceed the atrial-sensed event threshold triggering steps 806 and 808. If the P-wave frequency still remains below the detection threshold, then the high frequency of A-pulses detected at step 810 are likely due to factors other than an underlying atrial tachycardia.

Thus, FIG. 18 provides a technique for determining whether an actual atrial tachycardia has occurred while the device is in non-tracking mode. Although not shown in the figure, after the atrial sensitivity is increased at step 812 to search for low-amplitude P-waves, the sensitivity is eventually reset to its normal level. This occurs at step 808 (if atrial tachycardia is detected based on the low-amplitude P-waves) or it occurs the next time step 810 is performed (if atrial tachycardia is not detected despite the increased atrial sensitivity.) Also, depending up on the implementation, the sensitivity adjustment technique of the figure may be performed either 1) continuously while in a non-tracking mode (i.e. the device continuously monitors P-wave frequency); 2) periodically while in a non-tracking mode (e.g. every five minutes); or 3) only when triggered to do so by some other event (e.g. only when a pattern-based analysis indicates a possible underlying tachycardia.) As with the other techniques described herein, a wide range of implementations may be provided consistent with the general principles of the invention.

What have been described are various exemplary techniques performed by an implantable cardiac stimulation device for improving the specificity of AMS and for detecting atrial tachycardias. Modifications can be made thereto without departing from the spirit and scope of the invention.

What is claimed is:

1. In an implantable cardiac stimulation device, a method comprising:
   detecting intrinsic atrial events based on an initial atrial sensitivity level;
   selectively delivering atrial pacing pulses to at least one atrium and monitoring for loss of capture of the atrial pacing pulses;
   increasing the atrial sensitivity level upon detecting a predetermined number of losses of capture and monitoring for lower-amplitude atrial events;
   if lower amplitude atrial events are detected, determining whether the lower amplitude atrial events are true intrinsic atrial events;
   if lower-amplitude atrial events are not detected, resetting the atrial sensitivity to the initial value; and
   controlling selected functions of the device based on any true intrinsic atrial events;
   wherein the device is capable of automatically switching between a tracking mode and a non-racking mode and wherein controlling selected functions of the device further comprises:
   determining a filtered atrial rate interval (FARI value) based only on intrinsic atrial events; and
   controlling mode selection based on the FARI value.

2. The method of claim 1 wherein controlling mode selection based on the FARI value comprises:
   comparing the FARI value with an atrial tachycardia detection rate (ATDR) threshold;
   if the FARI value exceeds the ATDR threshold while the device is in the tracking mode, switching to the non-tracking mode; and
   if the FARI value falls below the ATDR threshold while the device is in the non-tracking mode, switching to the tracking mode.

3. The method of claim 2 wherein determining whether the lower amplitude atrial events are true intrinsic atrial events comprises:
   detecting ventricular events;
   determining a degree of variability to an interval between atrial events and ventricular events; and
   if the degree of variability exceeds a variability threshold, identifying the atrial events as intrinsic atrial events; and
   if the degree of variability falls below the variability threshold, ignoring the atrial events.

4. The method of method claim 1 wherein controlling selected functions of the device further comprises:
   inhibiting generation of atrial pacing pulses if the lower-amplitude atrial events are identified as true intrinsic atrial events due to possible atrial tachycardia.

5. In an implantable cardiac stimulation device, a pacing system comprising:
   an atrial sensing system operative to detect atrial events;
   an atrial pacing system operative to deliver atrial pacing pulses;
   an automatic capture detection system operative to detect loss of capture of the atrial pacing pulses; and
   an atrial tachycardia detection system operative to increase a sensitivity by which the atrial sensing system detects atrial events upon detection of a predetermined number of losses of capture and to detect atrial tachycardia based on lower amplitude atrial events detected using the increased sensitivity:
   wherein the system is capable of operating in a tracking mode and a non-tracking mode and wherein the system further includes:
   a filtered atrial rate interval (FARI) detection system operative to determine a filtered atrial rate based on only atrial-sensed events; and
   an automatic mode switching system operative to determine whether to switch tracking modes based on the FARI.

6. In an implantable cardiac stimulation device, a pacing system comprising:
   means for detecting atrial events;
   means for delivering atrial pacing pulses;
   means for detecting loss of capture of the atrial pacing pulses;
   means for increasing a sensitivity by which the atrial events are sensed upon detection of a predetermined number of losses of capture; and means for detecting atrial tachycardia based on lower amplitude atrial events detected using the increased sensitivity;
wherein the device is capable of automatically switching between a tracking mode and a non-tracking mode and wherein controlling selected functions of the device further comprises:

means for determining a filtered atrial rate interval (FARI value) based only on intrinsic atrial events; and
means for controlling mode selection based on the FARI value.

* * * * *